US008367069B2

(12) United States Patent
Ferris et al.

(10) Patent No.: US 8,367,069 B2
(45) Date of Patent: Feb. 5, 2013

(54) CYTOTOXIC T CELL DEFINED EGFR PEPTIDE AND AN OPTIMIZED DERIVATIVE PEPTIDE

(75) Inventors: Robert L. Ferris, Pittsburgh, PA (US); Pedro Andrade, Pittsburgh, PA (US); Andres Lopez-Albaitero, Pittsburgh, PA (US)

(73) Assignee: University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 12 days.

(21) Appl. No.: 12/959,073

(22) Filed: Dec. 2, 2010

(65) Prior Publication Data

US 2011/0171170 A1 Jul. 14, 2011

Related U.S. Application Data

(63) Continuation-in-part of application No. PCT/US2009/045986, filed on Jun. 2, 2009.

(60) Provisional application No. 61/058,056, filed on Jun. 2, 2008.

(51) Int. Cl.
| | |
|---|---|
| *C07K 11/00* | (2006.01) |
| *A61K 39/39* | (2006.01) |
| *A61K 38/08* | (2006.01) |
| *A61K 39/12* | (2006.01) |
| *C07K 14/71* | (2006.01) |

(52) U.S. Cl. ............ 424/185.1; 514/19.3; 514/21.6; 514/939; 530/328; 424/184.1; 424/204.1; 424/277.1; 423/556; 423/303

(58) Field of Classification Search .................... None
See application file for complete search history.

(56) References Cited

U.S. PATENT DOCUMENTS

| | | | |
|---|---|---|---|
| 4,235,871 A | | 11/1980 | Papahadjopoulos et al. |
| 4,501,728 A | | 2/1985 | Geho et al. |
| 4,837,028 A | | 6/1989 | Allen |
| 5,019,369 A | | 5/1991 | Presant et al. |
| 5,648,226 A | | 7/1997 | Van den Eynde et al. |
| 5,750,395 A | | 5/1998 | Fikes et al. |
| 5,827,703 A | | 10/1998 | Debs et al. |
| 5,840,839 A | | 11/1998 | Wang et al. |
| 7,154,026 B2 | * | 12/2006 | Arioli et al. |
| 7,628,986 B2 | * | 12/2009 | Weber et al. |
| 7,763,452 B2 | | 7/2010 | Eskling et al. |
| 7,767,792 B2 | | 8/2010 | Johns et al. |
| 7,786,261 B2 | * | 8/2010 | De Crescenzo et al. |
| 2005/0222059 A1 | | 10/2005 | Tang |
| 2005/0255555 A1 | | 11/2005 | Johns et al. |
| 2006/0240511 A1 | | 10/2006 | Eskling et al. |
| 2007/0248628 A1 | * | 10/2007 | Keller et al. |
| 2008/0090233 A1 | * | 4/2008 | Garcia et al. |

OTHER PUBLICATIONS

UniProtKB/Swiss-Prot [online], accession Q9LR92, T23E23.18, Oct. 13, 2006 [retrieved on Apr. 26, 2012]. Retrieved from the Internet: <http://www.ncbi.nlm.nih.gov/protein/75335357>.*

(Continued)

*Primary Examiner* — Claire Kaufman
(74) *Attorney, Agent, or Firm* — Leydig, Voit & Mayer, Ltd.

(57) ABSTRACT

The invention provides a polypeptide having a sequence of amino acids consisting of IXDFGLAKL (SEQ ID NO: 1), as well as a nucleic acid encoding the polypeptide, vector comprising the nucleic acid, cell comprising the vector, and compositions thereof. The invention also provides a method of inducing a T-cell response in a patient with epithelial cancer, and a method inhibiting epithelial cancer, wherein the methods comprise administering the composition of the invention. The invention further provides a method of stimulating a cell with the inventive polypeptide and a cell so stimulated.

10 Claims, 17 Drawing Sheets

OTHER PUBLICATIONS

Andrade Filho et al., "Novel Immunogenic HLA-A0201-restricted Epidermal Growth Factor Receptor-specific T-cell Epitope in Head and Neck Cancer Patients," *J. Immunother.*, 33(1): 83-91 (Jan. 2010).

Baxby et al., "Potential use of non-replicating vectors as recombinant vaccines," *Vaccine*, 10(1): 8-9 (1992).

Chen et al., "A testicular antigen aberrantly expressed in human cancers detected by autologous antibody screening," *Proc. Natl. Acad. Sci. USA*, 94: 1914-1918 (Mar. 1997).

Cohen et al., "Nucleotide sequence of the cDNA encoding human tyrosinase-related protein," *Nucleic Acids Research*, 18(9): 2807-2808 (1990).

Davison et al., "Structure of Vaccinia Virus Early Promoters," *J. Mol. Biol.*, 210: 749-769 (1989).

Deluca et al., "Parenteral Drug-Delivery Systems," *Pharmaceutics and Pharmacy Practice*, (Banker et al., eds.) 238-250 (J. B. Lippincott Co., Philadelphia, PA, 1982).

Gritz et al., Generation of Hybrid Genes and Proteins by Vaccinia Virus-Mediated Recombination: Application to Human Immunodeficiency Virus Type 1 env,: *Journal of Virology*, 64(12): 5948-5957 (Dec. 1990).

Hollstein et al., "Database of p53 gene somatic mutations in human tumors and cell lines," *Nucleic Acids Research*, 22(17): 3551-3555 (1994).

Israeli et al., "Molecular Cloning of a Complementary DNA Encoding a Prostate-specific Membrane Antigen," *Cancer Research*, 53: 227-230 (Jan. 15, 1993).

Jackson et al., "A second tyrosinase-related protein, TRP-2, maps to and is mutated at the mouse slaty locus," *The EMBO Journal*, 11(2): 527-535 (1992).

Jenkins et al., "Formation of Lentivirus Particles by Mammalian Cells Infected with Recombinant Fowlpox Virus," *Aids Research and Human Retroviruses*, 7(12): 991-998 (1991).

Kaufman et al., "A Recombinant Vaccinia Virus Expressing Human Carcinoembryonic Antigen (CEA)," *Int. J. Cancer*, 48: 900-907 (1991).

Kawakami et al., "Identification of the Immunodominant Peptides of the MART-1 Human Melanoma Antigen Recognized by the Majority of HLA-A2-restricted Tumor Infiltrating Lymphocytes," *The Journal of Experimental Medicine*, 180: 347-352 (Jul. 1994).

Kawakami et al., "Identification of a human melanoma antigen recognized by tumor-infiltrating lymphocytes associated with in vivo tumor rejection," *Proc. Natl. Acad. Sci. USA*, 91: 6458-6462 (Jul. 1994).

Korean Intellectual Property Office, International Search Report/Written Opinion with respect to PCT/US2009/045986 (Jan. 12, 2010).

Kwon et al., "Isolation and sequence of a cDNA clone for human tyrosinase that maps at the mouse c-albino locus," *Proc. Natl. Acad Sci.*, 84: 7473-7477 (Nov. 1987).

Lu et al., "Epidermal Growth Factor Receptor (EGFR) Ubiquitination as a Mechanism of Acquired Resistance Escaping Treatment by the Anti-EGFR Monoclonal Antibody Cetuximab," *Cancer Research*, 67(17): 8240-8247 (Sep. 1, 2007).

Moss, "Vaccinia Virus: A Tool for Research and Vaccine Development," *Science*, 252(5013): 1662-1667 (Jun. 21, 1991).

NCBI Nucleotide Database, "Human carcinoembryonic antigen mRNA (CEA), complete cds," Accession No. M29540.1 (Nov. 1, 1994). Retrieved on Jul. 6, 2011.

NCBI Protein Database, "Receptor tyrosine-protein kinase erbN-2," Accession No. P04626 (Nov. 2, 2010). Retrieved on Nov. 29, 2010.

Paoletti, "Applications of px virus vectors to vaccination: An update," *Proc. Natl. Acad. Sci. USA*, 93: 11349-11353 (Oct. 1996).

Perkus et al., "Recombinant Vaccinia Virus: Immunization Against Multiple Pathogens," *Science*, 229(4717): 981-984 (Sep. 6, 1985).

Ramakrishna et al., "Generation and Phenotypic Characterization of New Human Ovarian Cancer Cell Lines with the Identification of Antigens Potentially Recognizable by HLA-Restricted Cytotoxic T Cells," *Int. J. Cancer*, 73: 143-150 (1997).

Shir et al., "EGF Receptor-Targeted Synthetic Double-Stranded RNA Eliminates Glioblastoma, Breat Cancer, and Adenocarcinoma Tumors in Mice," *PLoS Medicine*, 3(1): 0125-0135 (Jan. 2006).

Shomura et al., "Identification of epidermal growth factor receptor-derived peptides immunogenic for HLA-A2$^+$ cancer patients," *British Journal of Cancer*, 90(8): 1563-1571 (2004).

Sutter et al., "Nonreplicating vaccinia vector efficiently expresses recombinant genes," *Proc. Natl. Acad. Sci. USA*, 89: 10847-10851 (Nov. 1992).

Szoka et al., "Comparative Properties and Methods of Preparation of Lipid Vesicles (Liposomes)," *Ann. Rev. Biophys. Bioeng.* 9: 467-508 (1980).

Trissel, "Intravenous Infusion Solutions," *ASHP Handbook on Injectable Drugs*, (Trissel, ed.) 622-646 (American Society of Hospital Pharmacists, Inc., Bethesda, MD, 1986).

\* cited by examiner

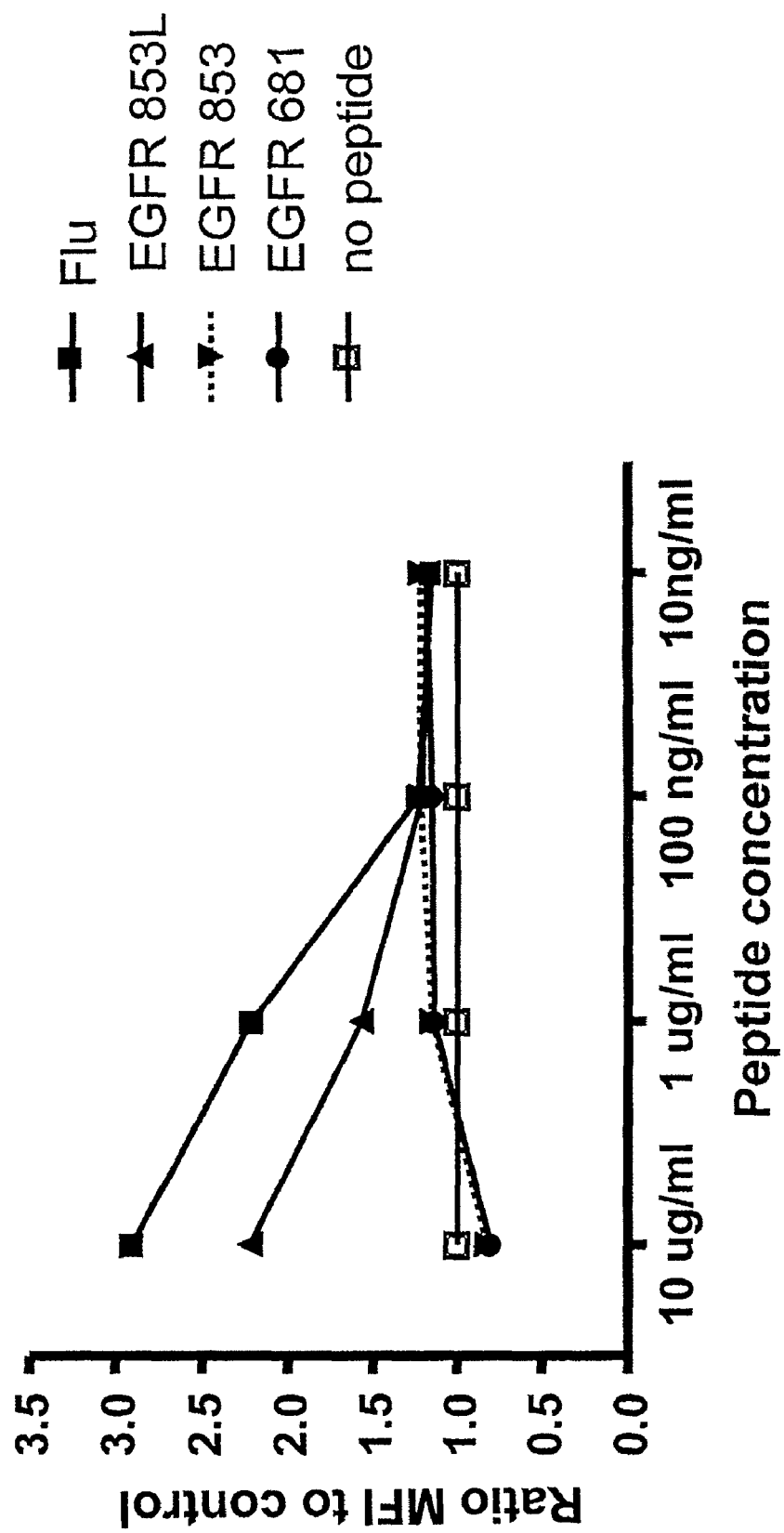

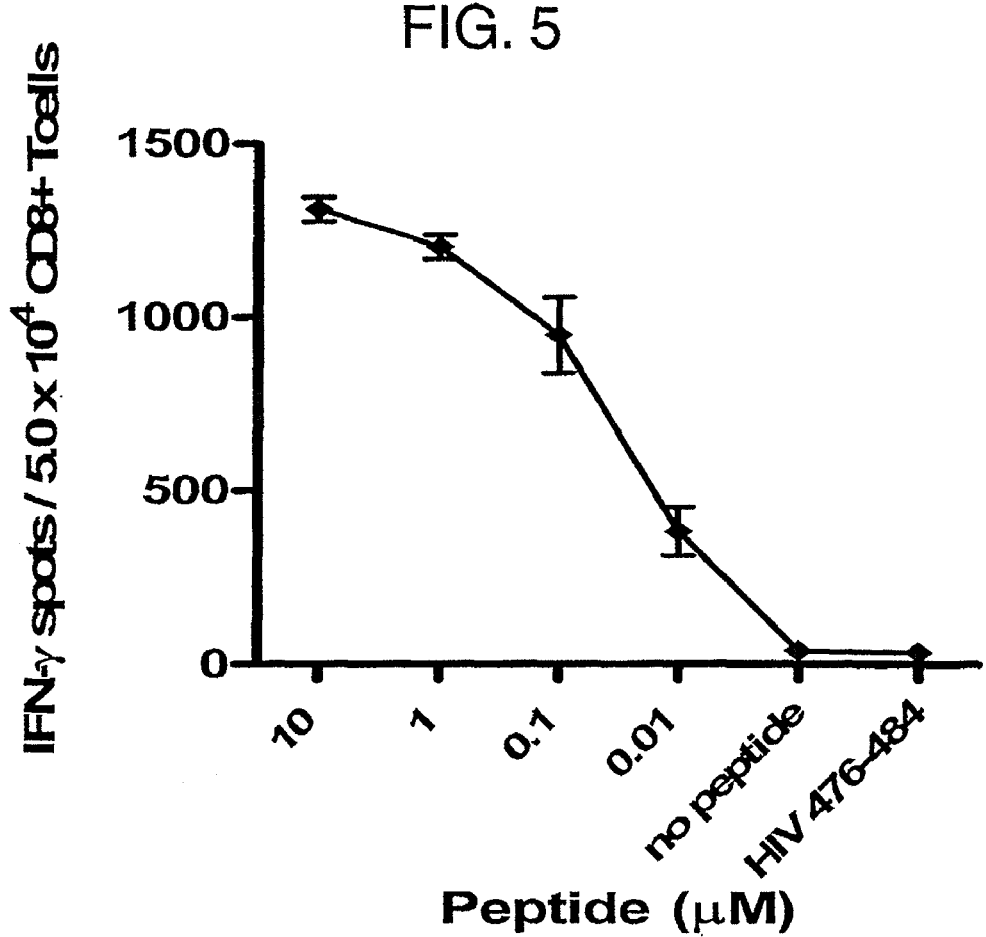

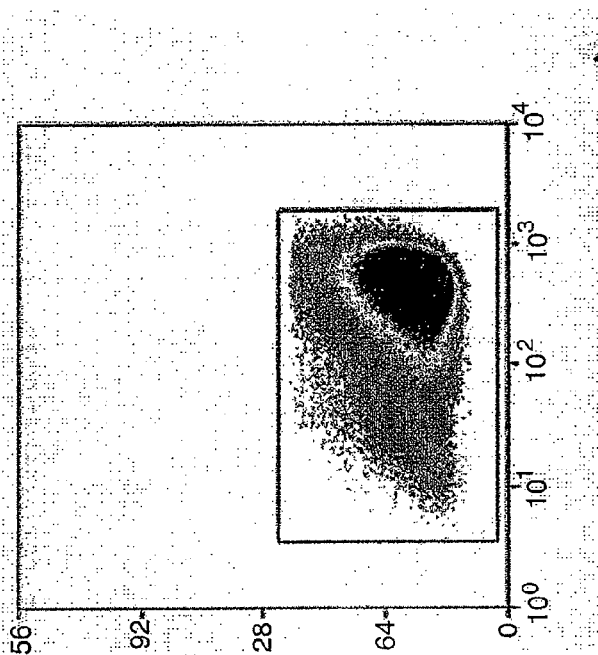

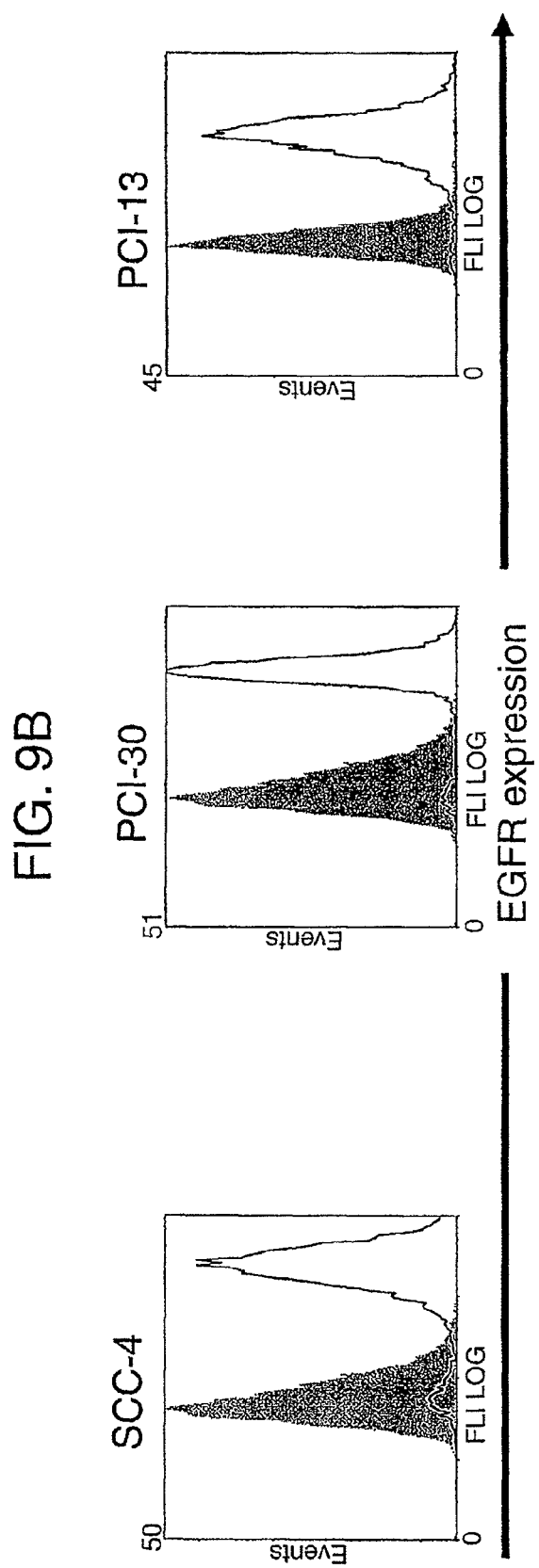

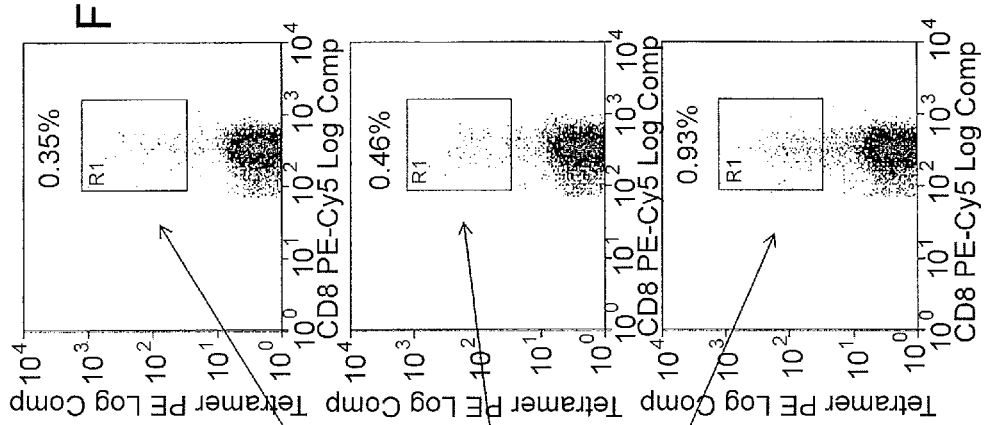
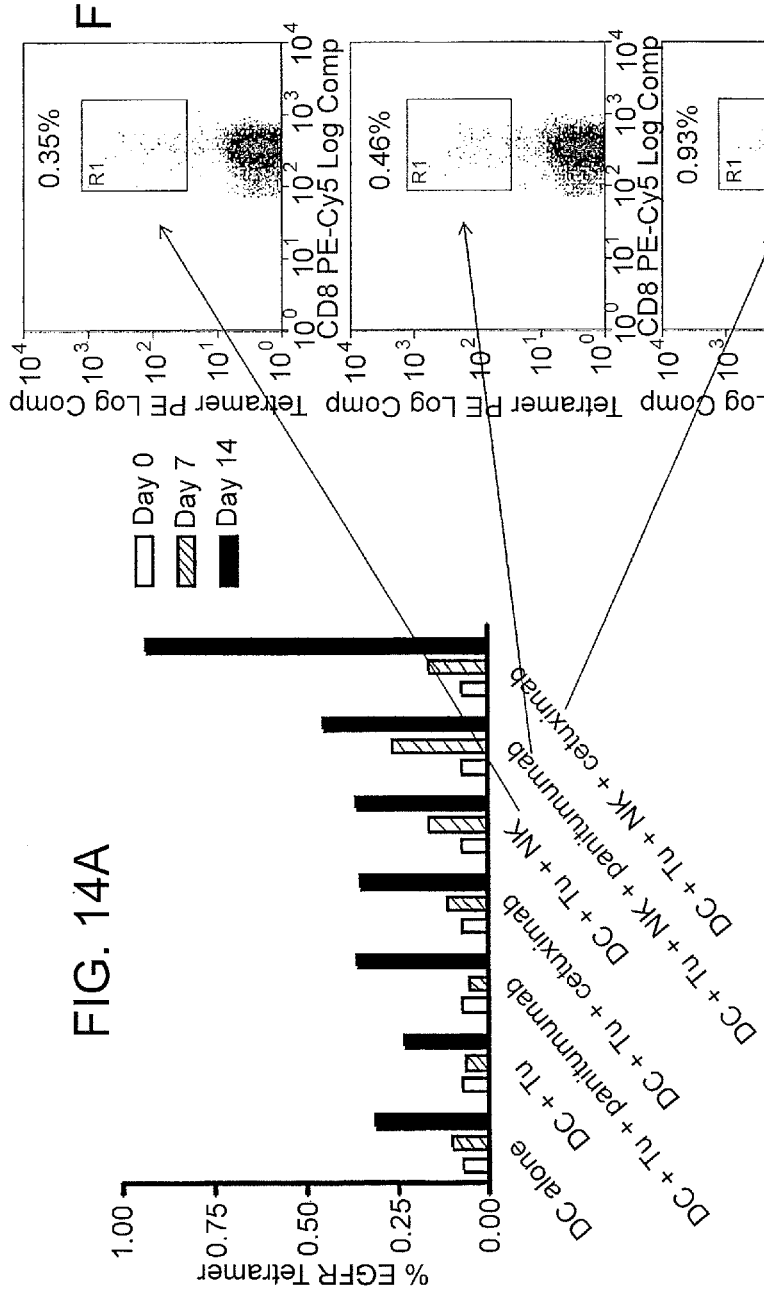
FIG. 14A
FIG. 14B

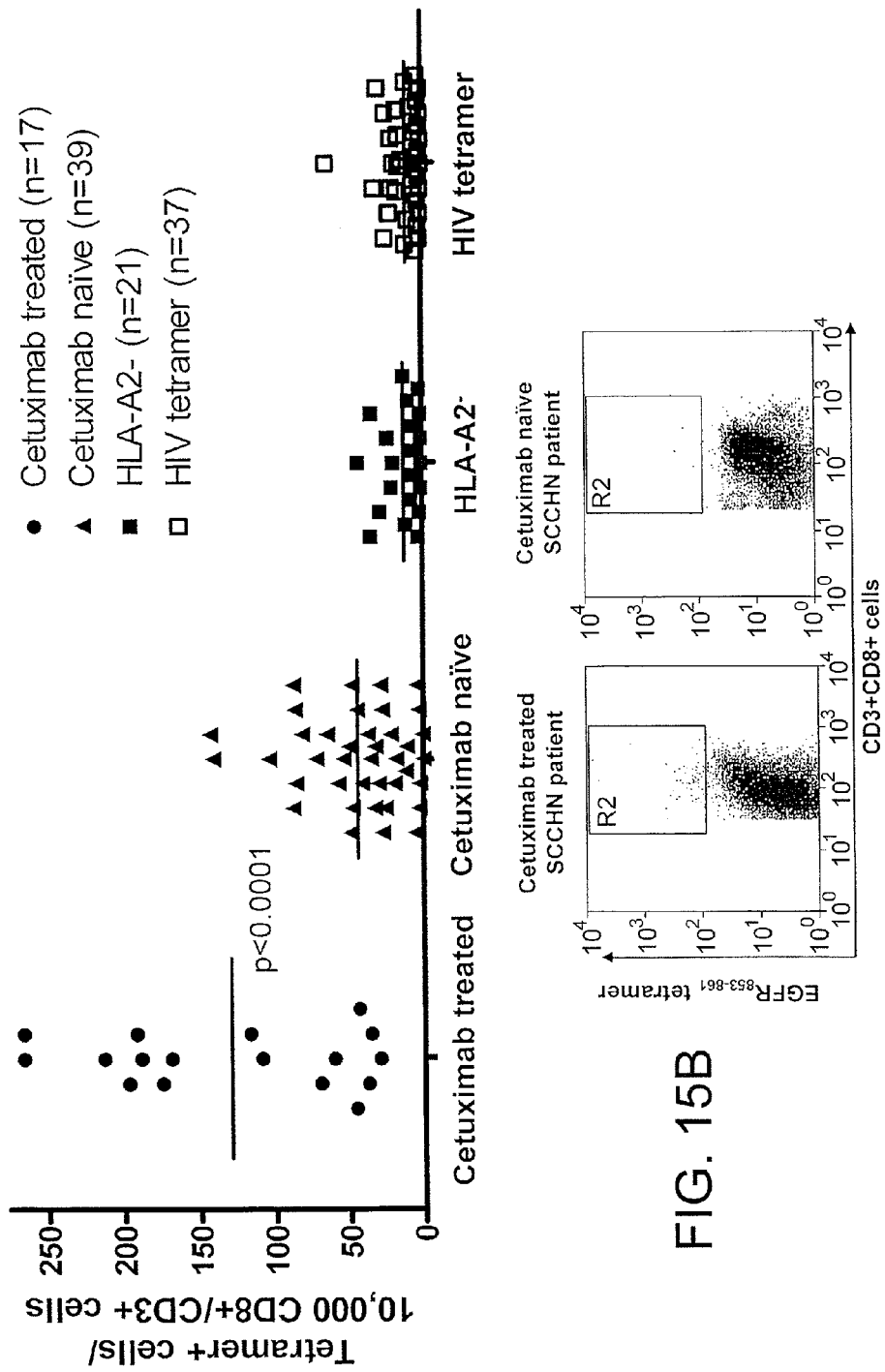

CYTOTOXIC T CELL DEFINED EGFR PEPTIDE AND AN OPTIMIZED DERIVATIVE PEPTIDE

CROSS-REFERENCE TO RELATED APPLICATIONS

This application is a continuation-in-part of co-pending International Patent Application PCT/US2009/045986, which was filed on Jun. 2, 2009, designating the United States, and which claims priority to U.S. Provisional Patent Application 61/058,056, which was filed on Jun. 2, 2008. The disclosures of these prior applications are incorporated herein in their entireties by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: 12.00 Kbytes ASCII (Text) file named "707233_ST25.txt," created on Dec. 2, 2010.

BACKGROUND OF THE INVENTION

The epidermal growth factor receptor (EGFR) is an attractive target for cancer therapy because it is highly overexpressed and correlated with poor prognosis in epithelial malignancies, including head and neck squamous cell carcinoma (HNSCC). Although clinical responses have been achieved using EGFR inhibition through blocking antibodies or EGFR tyrosine-kinase inhibitors, many individuals do not respond to these treatments. Thus, the desire exists for additional EGFR inhibition therapies.

BRIEF SUMMARY OF THE INVENTION

The invention provides a polypeptide having a sequence of amino acids consisting of IXDFGLAKL (SEQ ID NO: 1), as well as a nucleic acid encoding the polypeptide, vector comprising the nucleic acid, cell comprising the vector, and compositions thereof.

The invention also provides a method of inducing a T-cell response in a patient with epithelial cancer, and a method of inhibiting epithelial cancer. The methods comprise administering the above-described composition.

The invention further provides a method of stimulating a cell with the inventive polypeptide and a cell so stimulated.

BRIEF DESCRIPTION OF THE SEVERAL VIEWS OF THE DRAWING(S)

FIG. 1 depicts the results of an HLA-A*0201 stabilization assay by EGFR peptides and flu. The ratio of mean fluorescence intensity (MFI) relative to control is on the y axis and peptide concentration is on the x-axis. The graph represents results for (i) Flu$_{58\text{-}66}$ (Flu), (ii) EGFR$_{853\text{-}861}$, corresponding to SEQ ID NO: 1, wherein the second position is a leucine (EGFR 853L), (iii) EGFR$_{853\text{-}861}$, corresponding to SEQ ID NO: 1, wherein the second position is a threonine (EGFR 853), (iv) EGFR$_{681\text{-}689}$ (EGFR 681), and (v) no peptide.

FIGS. 2A, 2B, 3, and 4 depict the results of ELISPOT assays. The targets are indicated on the x-axis and the number of interferon-γ (IFN-γ) spots/5.0×10$^4$ CD8+ T cells is indicated on the y-axis for SCC4 (FIG. 2A), PCI-30 (FIG. 2B and FIG. 4), and PCI-13 (FIG. 3) cancer cells.

FIG. 5 depicts the results of an ELISPOT assay of CD8+ T cells from a healthy HLA:A0201 donor following three in vitro stimulations with the peptide EGFR$_{853}$ and challenge with T2 cells, T2 cells plus peptide (titrated), or T2 cells plus negative control peptide (HIV 476-484). The challenge material is indicated on the x-axis and the number of IFN-γ spots/ 5.0×10$^4$ CD8+ T cells is indicated on the y-axis.

FIGS. 6A and 6B depict the results of ELISPOT assays. The targets are indicated on the x-axis and the number of IFN-γ spots/5.0×10$^4$ CD8+ T cells is indicated on the y-axis. The HLA-A, -B, and -C specific monoclonal antibody (mAb) W6/32, HLA-A specific mAb LGIII, and the HLA-DR specific mAb L.243 were used to determine class I restricted activity and specificity with wild-type peptide EGFR$_{853}$ (FIG. 6A) and the optimized peptide EGFR$_{853L}$ (FIG. 6B).

FIGS. 8A-8D depict the HLA-A2 peptide EGFR$_{853}$ and EGFR$_{853L}$ tetramer-sorted population of healthy donor stained after in vitro expansion.

Figure 9A:
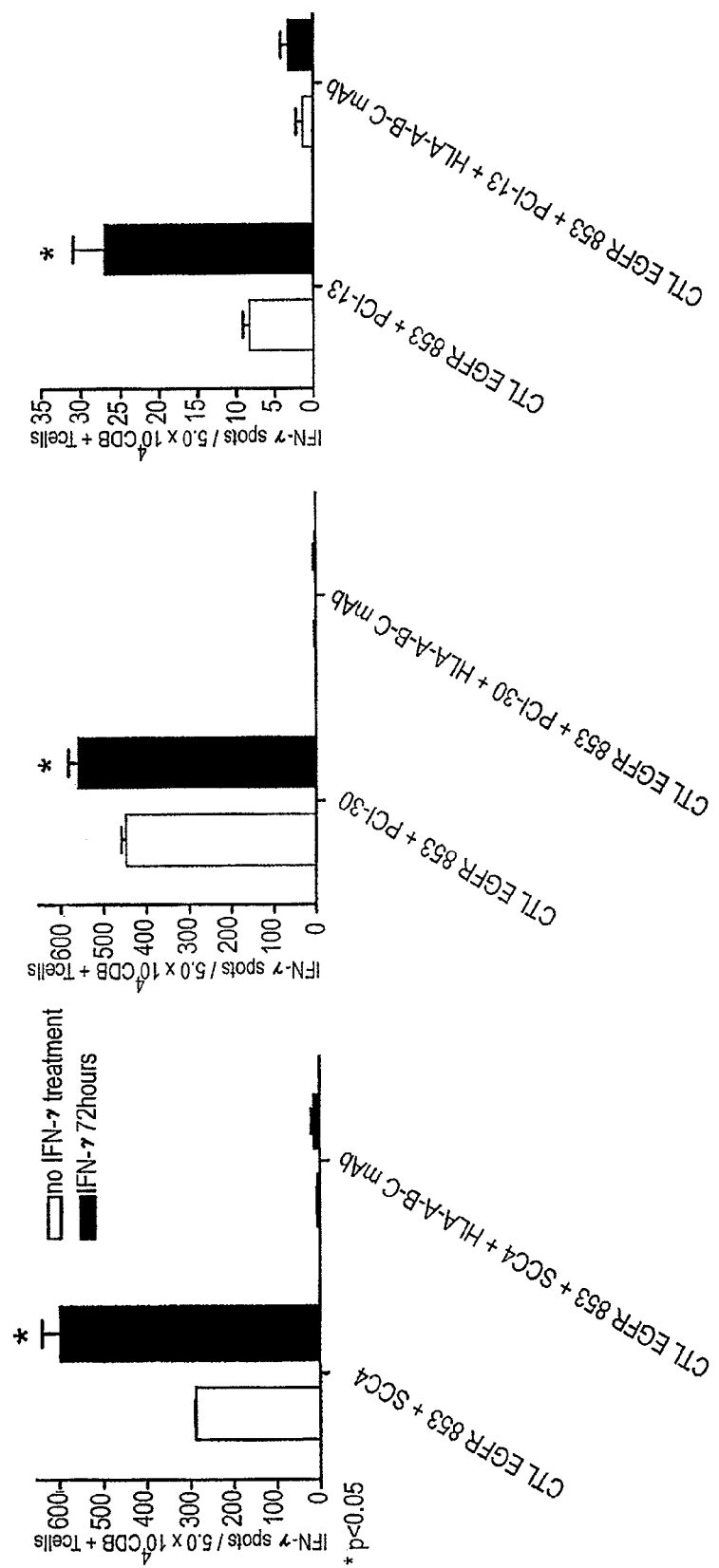

FIG. 9A depicts the results of ELISPOT assays. EGFR$_{853}$ peptide-specific CD8+ T cells recognize three Head and Neck cell lines (SCC-4, PCI-30, and PCI-13), which recognition was blocked by anti-HLA Class I mAb (FIG. 9A). The targets are indicated on the x-axis and the number of IFN-γ spots/ 5.0×10$^4$ CD8+ T cells is indicated on the y-axis. FIG. 9B depicts the EGFR expression of the three Head and Neck cell lines (SCC-4, PCI-30, and PCI-13) using flow-cytometry with cetuximab.

Figure 10:
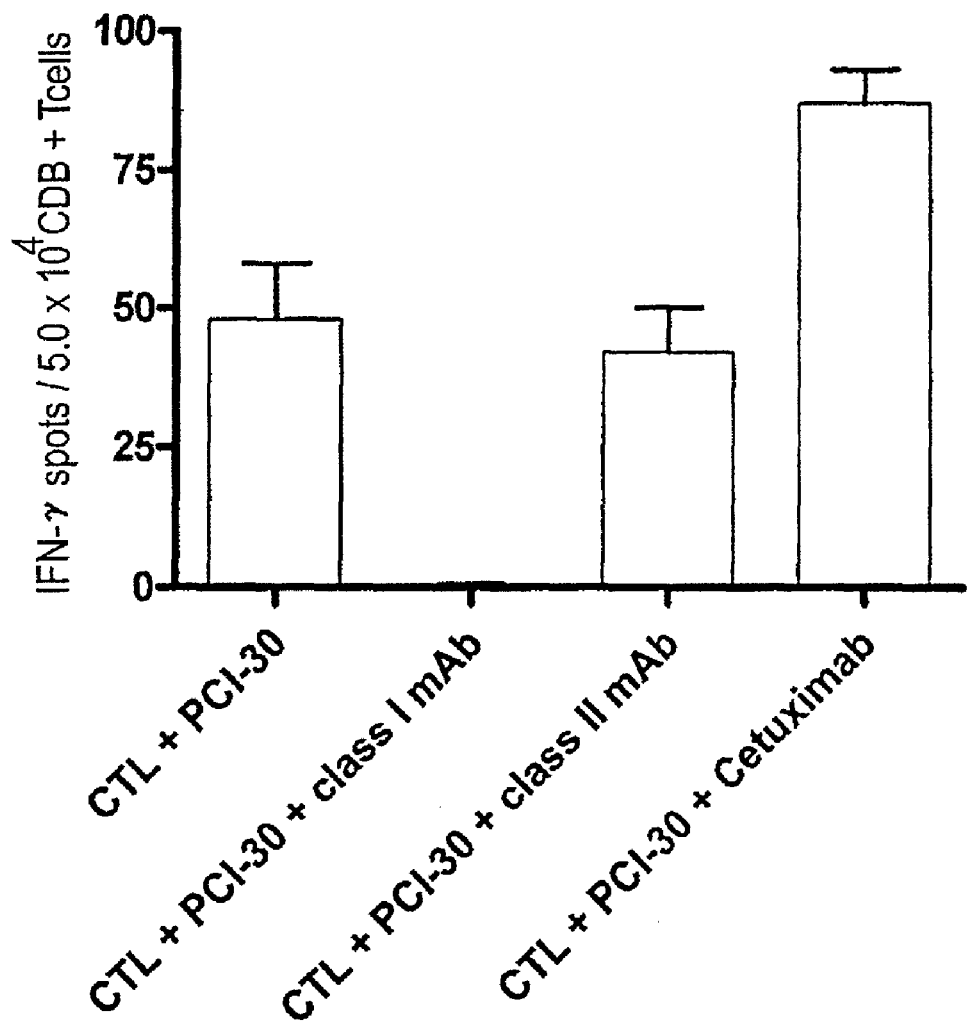

FIG. 10 depicts the results of an ELISPOT assay. EGFR$_{853}$ peptide-specific CD8+ T cells recognize PCI-30, which recognition was (i) blocked by anti-HLA Class I mAb but not by anti-HLA Class II mAb and (ii) increased after treatment with cetuximab. The targets are indicated on the x-axis and the number of IFN-γ spots/5.0×10$^4$ CD8+ T cells is indicated on the y-axis.

Figure 11:
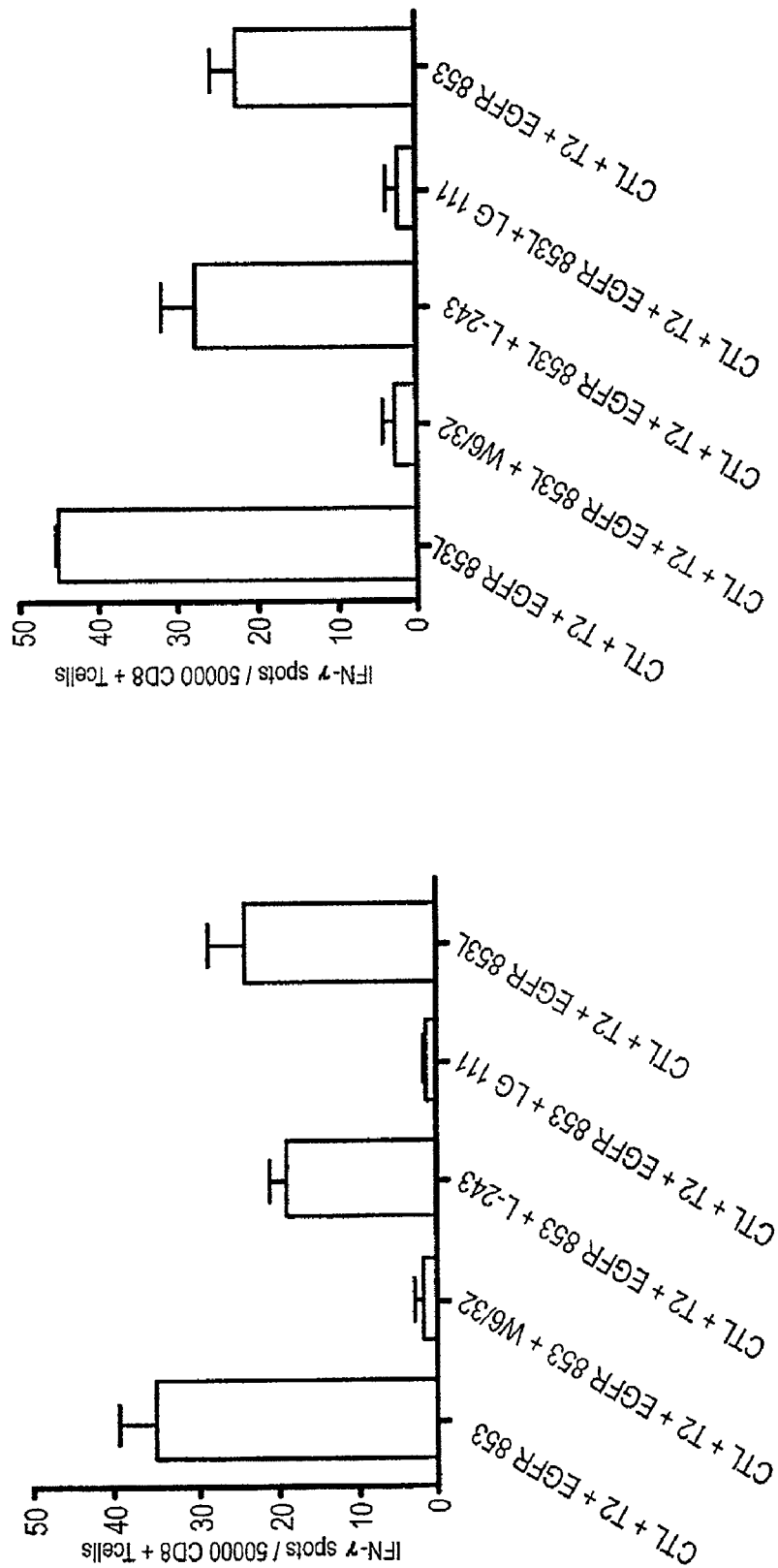

FIG. 11 depicts the results of an ELISPOT assay of CD8+ T cells from a healthy HLA:A0201 donor following three in vitro stimulations with the peptide EGFR$_{853}$ $_{or}$ EGFR$_{853L}$. The targets are indicated on the x-axis and the number of IFN-γ spots/5.0×10$^4$ CD8+ T cells is indicated on the y-axis.

Figure 12:
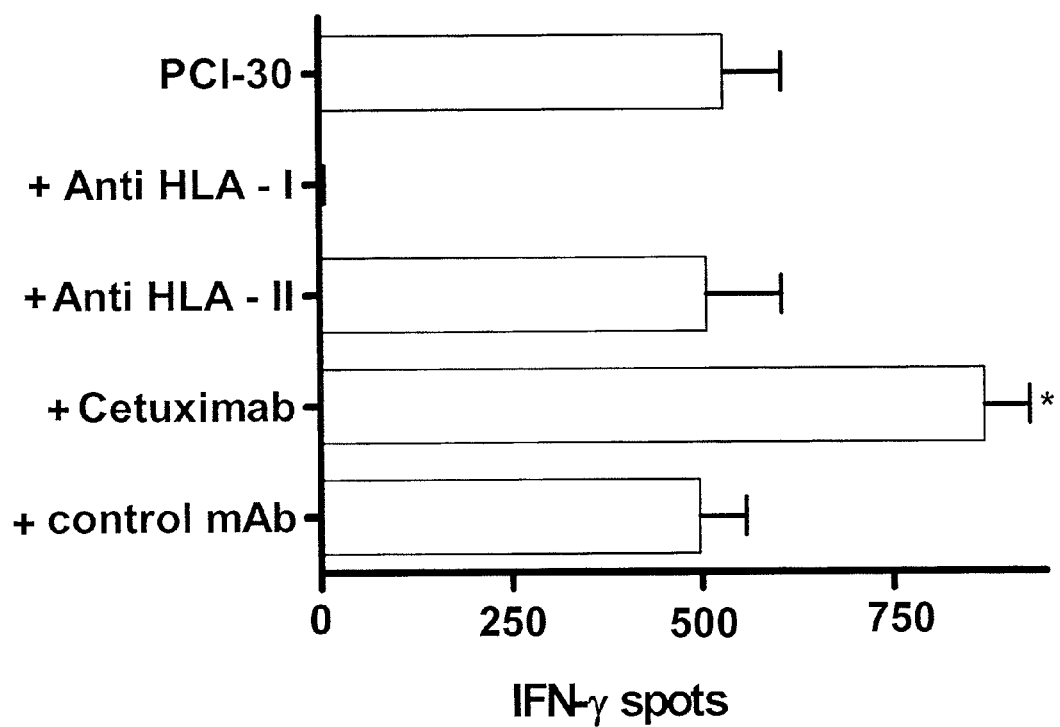

FIG. 12 is depicts the results of an ELISPOT assay. The targets are indicated on the y-axis and the number of interferon-γ (IFN-γ) spots is indicated on the x-axis. The "*" indicates a p value of ≦0.05, comparing CTL reactivity (50× 10$^4$ T cells) against PCI-30 cells incubated with cetuximab relative to PCI-30 cells incubated with a control IgG1 mAb (2-tailed permutation test).

Figure 13:
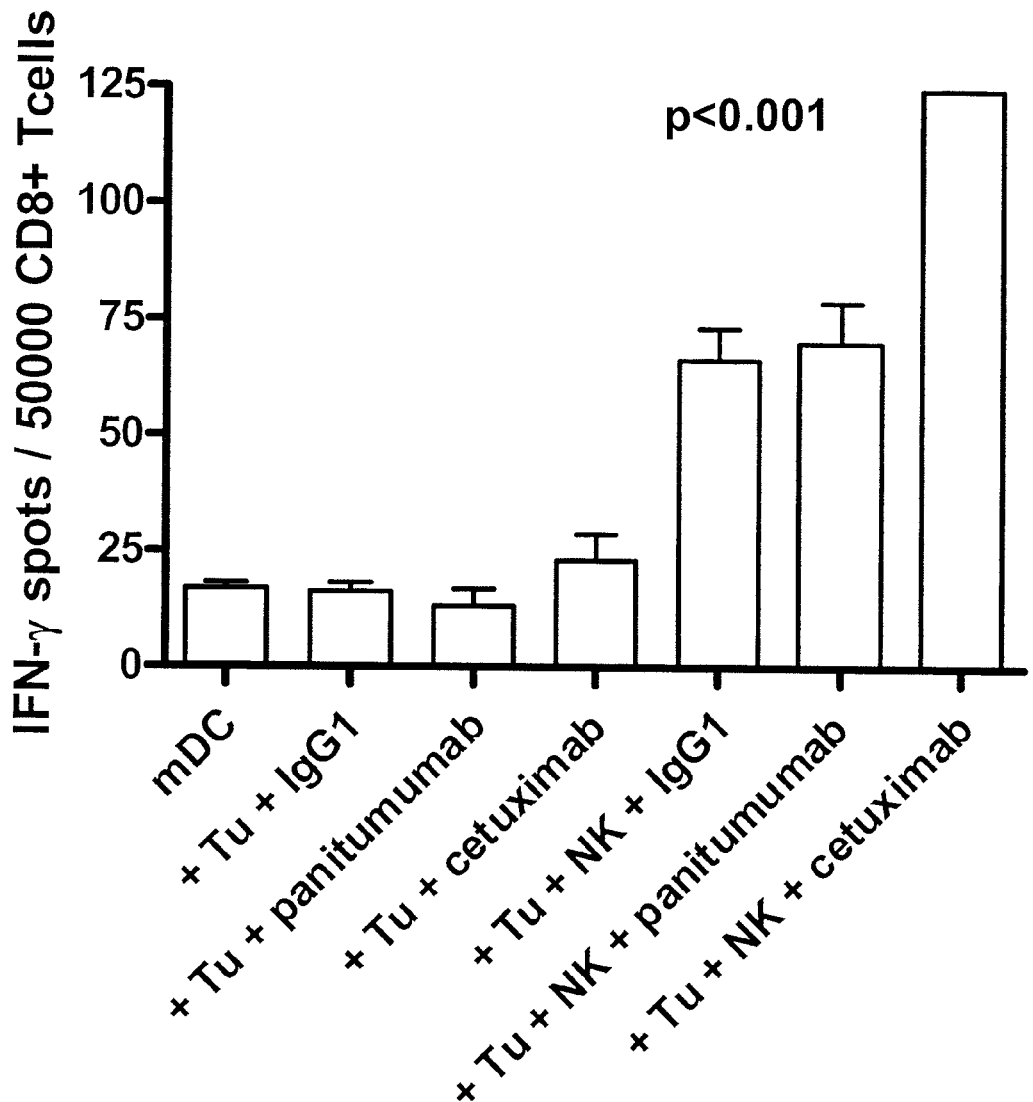

FIG. 13 depicts the results of an ELISPOT assay. The targets are indicated on the x-axis and the number of interferon-γ (IFN-γ) spots/5.0×10$^4$ CD8+ T cells is indicated on the y-axis.

FIG. 14A depicts the results of an ELISPOT assay. The challenge material is indicated on the x-axis and the percentage of EGFR tetramers at Day 0, 7, and 14 is indicated on the y-axis. FIG. 14B depicts the HLA-A2 peptide EGFR$_{853}$ tetramer-sorted population stained after in vitro expansion.

FIG. 15A depicts the results of a flow cytometry analysis to measure EGFR$_{853\text{-}861}$ tetramer staining of CD3+CD8+ T cells. PBMC were isolated from cetuximab-treated or cetuximab-naïve HNC patients, as well as HLA-A*0201-patients α-axis). A tetramer that binds to HIV-1 (pol$_{478\text{-}484}$)-specific T cells (from PBMC of cetuximab-treated or cetuximab-naïve HNC patients) was used as a negative control α-axis). The number of tetramer+ cells per 10,000 CD3+CD8+ cells is indicated on the y-axis. FIG. 15B depicts the HLA-A2 peptide EGFR$_{853}$ tetramer-sorted population stained after in vitro expansion.

DETAILED DESCRIPTION OF THE INVENTION

The invention provides a polypeptide having a sequence of amino acids consisting of IXDFGLAKL (SEQ ID NO: 1), wherein the X at position 2 can be leucine or threonine. IXDFGLAKL (SEQ ID NO: 1) corresponds to positions 853-861 of the epidermal growth factor receptor (EGFR) (see, e.g., GenBank Accession No. AY588246; and SEQ ID NO: 2). In one embodiment, the polypeptide is isolated or substantially purified.

The polypeptide having a sequence of amino acids consisting of IXDFGLAKL (SEQ ID NO: 1) is an immunogenic peptide with an HLA-A2 binding motif. In one embodiment, the polypeptide has a leucine at position 2 of SEQ ID NO: 1, which enhances HLA-A2 binding stimulation of anti-EGFR T cells. The invention also encompasses variants of SEQ ID NO: 1, which contain one, two, or three modifications (e.g., deletions, substitutions, or additions) of SEQ ID NO: 1. The variants of SEQ ID NO: 1 maintain the activity of the polypeptide of SEQ ID NO: 1, or have an increased activity, antigenicity, stability, or solubility.

In some applications, the polypeptide can elicit a cellular immune response against (i) an EGFR family member protein (e.g., EGFR) or a portion thereof, (ii) cells expressing an EGFR family member protein or portion thereof, and/or (iii) cells that bind an EGFR family member protein or a portion thereof. The EGFR (ErbB) family consists of four closely related receptor tyrosine kinases: EGFR (ErbB-1), HER2/c-neu (ErbB-2), Her 3 (ErbB-3), and Her 4 (ErbB-4). For example, in some applications, the polypeptide can generate cytotoxic T lymphocytes that inhibit or lyse (i) target cells that express or have bound thereto an EGFR family member protein (e.g., EGFR) or a portion thereof or (ii) target cells that express or have bound thereto one or more (e.g., two, three, four, five, six, seven, eight, nine, or ten) of the polypeptide of the invention.

The invention also provides a fusion polypeptide comprising one or more (e.g., two, three, four, five, six, seven, eight, nine, or ten) polypeptides having a sequence of amino acids consisting of IXDFGLAKL (SEQ ID NO: 1), which, optionally, can be joined by an amino acid linker sequence. Amino acid linker sequences are known in the art and can comprise about one to about ten (e.g., two, three, four, five, six, seven, eight, or nine) amino acids. The fusion polypeptide also can comprise other helper peptides or carrier molecules to enhance the immunogenicity of the polypeptide. Such molecules include, but are not limited to, an influenza peptide, tetanus toxoid, tetanus toxoid CD4 epitope, *Pseudomonas* exotoxin A, and poly-L-lysine.

The polypeptides of the invention can be obtained by any suitable methods, including, but not limited to, recombinant nucleic acid technology, chemical peptide synthesis, and protease cleavage of isolated EGFR.

The invention also provides an isolated nucleic acid comprising a sequence that encodes a polypeptide of the invention. The nucleic acid can be single or double stranded and can include DNA or RNA molecules (e.g., DNA, DNA/DNA, RNA, or RNA/DNA). The nucleic acid encompasses variants containing one or more (e.g., two, three, four, or five) substitutions, deletions, or additions that maintain or increase the ability of the polypeptide to elicit a cellular immune response against EGFR family member protein or portion thereof or against cells expressing or binding an EGFR family member protein or portion thereof. The nucleic acid can be derived from a variety of sources including genomic DNA, cDNA, synthetic DNA, synthetic RNA, or combinations thereof. In one embodiment, the nucleic acid is isolated or substantially purified.

Isolated refers to material (e.g., a polypeptide or nucleic acid) that is largely free from components which normally accompany or interact with it as found in its naturally occurring environment, or if in its natural environment, the material has been non-naturally altered to a composition. In the case of a nucleic acid, an isolated nucleic acid refers to a nucleic acid placed at a locus in the cell not native to a material found in that environment. The isolated material optionally comprises material not found with the material in its natural environment. For example, a naturally occurring nucleic acid becomes an isolated nucleic acid if it is altered, or if it is transcribed from DNA which is altered, by non-natural, synthetic methods performed within the cell from which it originates.

Similarly, substantially purified refers to material (e.g., a polypeptide or nucleic acid) that is considerably (e.g., about 60%, about 65%, about 70%, about 75%, about 80%, about 85%, about 90%, about 95%, about 96%, about 97%, about 98%, or about 99%) free from contaminants or materials that accompany or interact with it as found in its naturally occurring environment.

The nucleic acid can be in the form of a vector. Any suitable vector can be used, including, but not limited to, bacterial vectors, viral vectors, and nucleic acid-based vectors. Viral vectors include, but are not limited to, poxvirus, Herpes virus, lentivirus, adeno-associated virus, alphavirus, retrovirus, picornavirus, and iridovirus.

Preferably, the vector is a poxvirus. Examples of poxviruses include replicating and non-replicating vectors, such as *orthopox* (e.g., vaccinia, raccoon pox, and rabbit pox), avipox (e.g., canarypox, pigeonpox, and fowlpox), suipox (e.g., swinepox), and capripox (e.g., goatpox and sheeppox). In particular, poxviruses can be selected from the group consisting of vaccinia-Copenhagen, vaccinia-Wyeth strain, vaccinia-MVA strain, NYVAC, fowlpox, TROVAC, canarypox, ALVAC, and swinepox. Parental poxviruses useful in constructing the recombinant poxvirus include, but are not limited to, *orthopox* virus such as replicating vaccinia virus (see, e.g., Perkus et al., *Science,* 229: 981-984 (1985); Kaufman et al., *Int. J. Cancer,* 48: 900-907 (1991); and Moss, *Science,* 252: 1662 (1991)), highly attenuated vaccinia viruses such as MVA, modified vaccinia Ankara (see, e.g., Sutter et al., *Proc. Nat'l Acad. Sci. U.S.A.,* 89: 10847-10851 (1992)), vaccinia-Copenhagen and NYVAC, avipoxviruses, such as fowlpox virus, canarypox virus, such as ALVAC (see, e.g., Baxby et al., *Vaccine,* 10: 8-9 (1992); and Paoletti, *Proc. Nat'l Acad. Sci. USA,* 93: 11349-11353 (1996)), and suipoxvirus, and capripoxvirus.

In one embodiment, the poxvirus is a vaccinia virus, such as a Wyeth strain or derivative thereof. A derivative of the Wyeth strain includes, but is not limited to, vTBC33. In yet another embodiment, the virus is Dry-Vax, which is available as a smallpox vaccine from the Centers for Disease Control, Atlanta, Ga. In another embodiment, the poxvirus is a strain of fowlpox, such as PDXVAC-TC (Schering-Plough Corporation).

The vector comprises at least one expression control element operably linked to the nucleic acid sequence. The expression control elements are inserted in the vector to control and regulate the expression of the nucleic acid sequence (see, e.g., Ausubel et al, 1987, in *Current Protocols in Molecular Biology*, John Wiley and Sons, New York, N.Y.). Expression control elements are known in the art (e.g., promoters). Promoters useful in the vector include, but are not limited to, poxyiral promoters, such as 30K, I3, sE/L, 7.5K, 40K, C1, and those described in the art (see, e.g., Davison et al., *J. Mol. Biol.,* 210: 749 769, (1989)).

When the vector is a nucleic acid-based vector, the constructs can be DNA or RNA or associated with/or encapsulated in a lipid carrier (e.g., a liposome). Liposomes can serve to target a nucleic acid or polypeptide to a particular tissue. Liposomes also can be used to increase the half-life of a nucleic acid or polypeptide. Many methods are available for preparing liposomes, as described in, for example, Szoka et al., *Ann. Rev. Biophys. Bioeng.,* 9, 467 (1980) and U.S. Pat. Nos. 4,235,871, 4,501,728, 4,837,028, and 5,019,369.

Naked DNA vectors can be prepared by methods described in the art (see, e.g., U.S. Pat. No. 5,827,703). The transcriptional initiation region, or promoter element, can be native to or homologous to the cell and/or to the DNA to be transcribed, or foreign or heterologous to the cell and/or the DNA sequence to be transcribed. Efficient promoter elements for transcription initiation of naked DNA include, but are not limited to, the SV40 early promoter, RSV promoter, adenovirus major late promoter, and CMV immediate early I promoter.

The vector is able to infect, transfect, or transduce a cell, which can be in vitro or within in a subject. The subject includes, but is not limited to, mammals (e.g., mice, rats, hamsters, guinea pigs, rabbits, cats, dogs, pigs, cows, horses, and primates, such as humans), birds, and fish. The cell can be any cell amenable to infection, transfection, or transduction by the vector and capable of expressing the foreign genes from the vector. Desirably, the cell includes, but is not limited to, professional antigen presenting cells (APCs) and antigen presenting precursor cells, such as monocytes, macrophages, dendritic cells (DCs), and Langerhans cells; lymphocytes (e.g., T cells, B cells, natural killer (NK) cells; a heat inactivated recombinant yeast cell; and an artificial antigen presenting construct.

The vector also desirably can infect, transfect, or transduce tumor cells or other cell types, such as fibroblasts or muscle cells. The cells express, or are engineered to express, the appropriate MHC (HLA) Class I or II molecules for appropriate antigenic presentation to $CD4^+$ and/or $CD8^+$ T cells. It will be understood that the invention provides a cell comprising a nucleic acid of the present invention.

The invention also provides a cell that has been stimulated with the inventive polypeptide. As discussed above, the cell includes, but is not limited to, professional antigen presenting cells (APCs) and antigen presenting precursor cells, such as monocytes, macrophages, dendritic cells (DCs), and Langerhans cells; lymphocytes (e.g., T cells, B cells, natural killer (NK) cells; a heat inactivated recombinant yeast cell; and an artificial antigen presenting construct. In one particular embodiment, the cell is a polypeptide-pulsed DC or T cell (e.g., CD8+ T cell) as described in Examples 5 and 6.

The cell that has been stimulated with the inventive polypeptide can be prepared by any suitable means. For example, as described in Examples 5 and 6, the inventive cell can be prepared by isolating a cell (e.g., an antigen presenting cell, such as a DC) from a sample (e.g., a blood or tissue sample) and pulsing the cell with the inventive polypeptide. The preparation method also can comprise the addition of adjuvants, such as cytokines (e.g., IL-1-beta, IL-2, IL-4, IL-6, IL-7, TNF-alpha, and PGE). Alternatively, the cell can be prepared by stimulating a cell (e.g., a lymphocyte, such as a T cell) with an antigen presenting cell that has been pulsed with the inventive polypeptide. Additional means for introducing the inventive polypeptide to a cell include the use of microparticles, microspheres, nanoparticules, and fusion of the polypeptide to a targeted delivery agent (e.g., an antibody that targets proteins expressed on T cells or tumor cells).

The cell that has been stimulated with the inventive polypeptide can be used to stimulate an immune response against an EGFR family member (e.g., EGFR or HER2). Accordingly, the invention provides a method of stimulating an immune response against an EGFR family member by administering (e.g., in vitro, ex vivo, or in vivo) the inventive cell (e.g., to a sample, such as blood or tissue sample, or to a patient, such as a cancer patient).

A polypeptide, nucleic acid, vector, or cell of the invention can be administered alone or in a composition (e.g., pharmaceutically acceptable composition). The composition of the invention comprises a carrier (e.g., a pharmaceutically acceptable carrier), such as those known in the art. The pharmaceutically acceptable carrier (or excipient) is preferably one that is chemically inert to the polypeptide, nucleic acid, vector, or cell and one that has no detrimental side effects or toxicity under the conditions of use. Such pharmaceutically acceptable carriers include, but are not limited to, water, saline, Cremophor EL (Sigma Chemical Co., St. Louis, Mo.), propylene glycol, polyethylene glycol, alcohol, and combinations thereof. The choice of carrier will be determined in part by the polypeptide, nucleic acid, vector, or cell, as well as by the particular method used to administer the composition. Accordingly, there is a wide variety of suitable formulations of the composition.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

A polypeptide, nucleic acid, vector, or cell of the invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. A polypeptide, nucleic acid, vector, or cell of the invention can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets.

A polypeptide, nucleic acid, vector, or cell of the invention can be administered as an injectable formulation. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

Topical formulations, including those that are useful for transdermal drug release, are well known to those of skill in the art and are suitable in the context of the invention for application to skin.

A polypeptide, nucleic acid, vector, or cell of the invention can be administered as a suppository by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

The concentration of a polypeptide, nucleic acid, vector, or cell of the invention in the pharmaceutical formulations can vary, e.g., from less than about 1%, usually at or at least about 10%, to as much as 20% to 50% or more by weight, and can be selected primarily by fluid volumes, and viscosities, in accordance with the particular mode of administration selected.

Methods for preparing administrable (e.g., parenterally administrable) polypeptides, nucleic acids, vectors, cells, and compositions thereof are known or apparent to those skilled in the art and are described in more detail in, for example, *Remington's Pharmaceutical Science* (17th ed., Mack Publishing Company, Easton, Pa., 1985).

The composition can comprise an adjuvant. The adjuvant can be any suitable adjuvant, such as those described in the part. For example, the adjuvant can be selected from the group consisting of but not limited to, interleukin (IL)-1-beta, IL-2, IL-4, IL-6, IL-7, IL-12, IL-15, IL-21, interferon (e.g., IFN-gamma), tumor necrosis factor (e.g., TNF-alpha), granulocyte macrophage colony stimulating factor (GM-CSF), incomplete Freund's adjuvant, alum, aluminum salts, aluminum phosphate, aluminum hydroxide, aluminum silica, Montanide, calcium phosphate, cyclophosphamide, and combinations thereof.

The composition can comprise a chemotherapeutic agent. The chemotherapeutic agent can be any suitable chemotherapeutic agent, such as those described in the art. For example, the chemotherapeutic agent can be selected from the group consisting of, but not limited to, alkylating agents, antimetabolites, anthracyclines, plant alkaloids, topoisomerase inhibitors, and other antitumor agents.

Preferably, the chemotherapeutic agent is an epidermal growth factor receptor (EGFR) family specific antibody. The EGFR family specific antibody can be any suitable antibody that recognizes one or more of the EGFR family (e.g., an EGFR-specific antibody, such as cetuximab and panitumumab). The antibody can be a monoclonal, polyclonal, human, and/or humanized antibody or an antibody fragment, such as $F(ab')_2$, Fab', Fv, and single chain Fv (scFv).

The composition can comprise a target antigen, which refers to an antigen or immunological epitope on the antigen that is crucial in immune recognition and ultimate elimination or control of the disease-causing agent or disease state in a mammal. The immune recognition can be cellular and/or humoral. In the case of intracellular pathogens and cancer, immune recognition is preferably a T lymphocyte response.

Target antigen includes an antigen associated with a pre-neoplastic or hyperplastic state. Such target antigen can be tumor specific antigen, tumor associated antigen (TAA), or tissue specific antigen, epitope thereof, and epitope agonist thereof. Examples of target antigens include, but are not limited to, carcinoembryonic antigen (CEA) and epitopes thereof such as CAP-1 and CAP-1-6D (see, e.g., GenBank Accession No. M29540), MART-1 (see, e.g., Kawakami et al., *J. Exp. Med.*, 180: 347 352 (1994)), MAGE-1 (see, e.g., U.S. Pat. No. 5,750,395), MAGE-3, GAGE (see, e.g., U.S.

Pat. No. 5,648,226), GP-100 (see, e.g., Kawakami et al., *Proc. Nat'l Acad. Sci. USA,* 91:6458-6462 (1992)), MUC-1, MUC-2, point mutated ras oncogene, normal and point mutated p53 oncogenes (see, e.g., Hollstein et al., *Nucleic Acids Res.,* 22: 3551-3555 (1994)), PSMA (see, e.g., Israeli et al., *Cancer Res.,* 53: 227-230 (1993)), tyrosinase (see, e.g., Kwon et al., *Proc. Nat'l. Acad. Sci. USA,* 84: 7473-7477 (1987)), TRP-1 (gp75) (see, e.g., Cohen et al., *Nucleic Acid Res.,* 18: 2807-2808 (1990) and U.S. Pat. No. 5,840,839), NY-ESO-1 (see, e.g., Chen et al., *Proc. Nat'l Acad. Sci. USA,* 94: 1914-1918 (1997)), TRP-2 (see, e.g., Jackson et al., *EMBO J,* 11:527 535 (1992)), TAG72, KSA, CA-125, PSA, HER-2/neu/c-erb/B2, BRC-I, BRC-II, bcr-abl, pax3-fkhr, ews-fli-1, HAGE, modifications of TAAs and tissue specific antigens, splice variants of TAAs, and epitope agonists. Preferably, the composition comprises one or more TAAs selected from the group consisting of MAGE (e.g., MAGE-1 or MAGE-3), p53, Erb2, MUC-1, HAGE, and human papilloma virus.

The polypeptide, nucleic acid, vector, cell, and compositions thereof can be administered using any suitable method including, but not limited to, oral, aerosol, parenteral (e.g., subcutaneous, intravenous, intraarterial, intramuscular, intradermal, interperitoneal, and intrathecal), rectal, and vaginal administration.

The amount (e.g., therapeutically effective amount) of a polypeptide, nucleic acid, vector, cell, and compositions thereof of the invention to be administered depends on the compound used and the particular route of administration. For example, the polypeptide or composition thereof can be administered in a dose of about 0.5 mg to about 100 mg (e.g., 1 mg, 2 mg, 5 mg, 10 mg, 15 mg, 20 mg, 25 mg, 30 mg, 40 mg, 50 mg, 60 mg, 70 mg, 80 mg, or 90 mg) per kilogram body weight of the subject. Several doses can be provided over a period of weeks.

When the polypeptide, nucleic acid, vector, cell, or compositions thereof is administered with one or more additional therapeutic agents (e.g., chemotherapeutic agents, adjuvants, or target antigens), the polypeptide, nucleic acid, vector, cell, or compositions thereof and one or more additional therapeutic agents can be coadministered. By "coadministering" is meant administering one or more additional therapeutic agents and the polypeptide, vector, or cell sufficiently close in time such that the polypeptide, nucleic acid, cell, vector, cell, or compositions thereof can enhance the effect of one or more additional therapeutic agents. In this regard, the polypeptide, vector, or cell can be administered first and the one or more additional therapeutic agents can be administered second, or vice versa. Alternatively, the polypeptide, nucleic acid, vector, cell, or compositions thereof and the one or more additional therapeutic agents can be administered simultaneously either in separate or combined compositions.

In one embodiment, the polypeptide, nucleic acid, vector, cell, or compositions thereof is administered with an EGFR-specific antibody, such as cetuximab. The antibody can be administered simultaneously or sequentially relative to the administration of the polypeptide, nucleic acid, vector, cell, or compositions thereof. When the antibody and the polypeptide, nucleic acid, vector, cell, or compositions thereof is administered with are administered sequentially, the antibody can be administered before (e.g., about 1 hour before, about 2 hours before, about 3 hours before, about 4 hours before, about 5 hours before, about 6 hours before, about 7 hours before, about 8 hours before, about 9 hours before, about 10 hours before, about 12 hours before, about 15 hours before, about 20 hours before, about 1 day before, about 2 days before, about 3 days before, about 1 week before, about 2 weeks before, or about 1 month before) the polypeptide, nucleic acid, vector, cell, or compositions thereof. Alternatively, the antibody can be administered after (e.g., about 1 hour after, about 2 hours after, about 3 hours after, about 4 hours after, about 5 hours after, about 6 hours after, about 7 hours after, about 8 hours after, about 9 hours after, about 10 hours after, about 12 hours after, about 15 hours after, about 20 hours after, about 1 day after, about 2 days after, about 3 days after, about 1 week after, about 2 weeks after, or about 1 month after) the polypeptide, nucleic acid, vector, cell, or compositions thereof.

The amount (e.g., therapeutically effective amount) of the antibody to be administered simultaneously or sequentially with the polypeptide, nucleic acid, vector, cell, or compositions thereof depends on the antibody used and the particular route of administration. For example, the antibody can be administered in a dose of about 0.5 mg to about 400 mg (e.g., 1 mg, 2 mg, 5 mg, 10 mg, 15 mg, 20 mg, 25 mg, 30 mg, 40 mg, 50 mg, 60 mg, 70 mg, 80 mg, 90 mg, 100 mg, 200 mg, or 300 mg). The antibody can be administered once or multiple times (e.g., two, three, four, five, or more times).

Interestingly, a subset of EGFR-specific antibody (cetuximab)-treated patients have enhanced numbers of $EGFR_{853}$-specific T cells (e.g., as compared to healthy individuals). The higher the numbers of $EGFR_{853}$-specific T cells, the less likely the patient is to have evidence of disease. Therefore, in addition to compositions and methods comprising an EGFR-specific antibody and the polypeptide, nucleic acid, vector, cell, or compositions thereof, the invention also encompasses compositions and methods comprising $EGFR_{853}$-specific T cells and the polypeptide, nucleic acid, vector, cell, or compositions thereof.

The vector or composition thereof (e.g., vaccine) can generate an immune response as a result of the administration of, for example, about $10^5$ to about $10^{10}$ (e.g., $10^6$, $10^7$, $10^8$, or $10^9$) pfu of the viral vector (e.g., poxvirus). The immune response can be boosted by administering additional antigen to the subject (e.g., in the form of a vector, polypeptide, or compositions thereof).

The invention also provides a method of inducing a T-cell response in a patient with epithelial cancer, comprising administering the composition of the invention to the subject, such that a T-cell response against the epithelial cancer is induced. In particular, the invention provides a method of generating EGFR-specific cytotoxic T lymphocytes (both in vivo and in vitro) by stimulation of lymphocytes with a polypeptide, nucleic acid, vector, cell, or compositions thereof of the invention, alone or in combination with one or more adjuvants, such as cytokines (e.g., IL-1-beta, IL-2, IL-4, IL-6, IL-7, IL-12, RANTES, GM-CSF, TNF-alpha, or IFN-gamma) or costimulatory molecules (e.g., B7.1, B7.2, ICAM-1, LFA-3, or CD72). The lymphocytes can be obtained from, for example, peripheral blood lymphocytes, tumor infiltrating lymphocytes, and lymph nodes.

The ability of the polypeptide, nucleic acid, vector, cell, or compositions thereof to generate and EGFR-specific cellular immune response can be determined by in vivo or in vitro parameters known in the art, such as antigen specific cytotoxicity assays, regression of $EGFR^+$ tumors, inhibition of $EGFR^+$ cancer cells, and the production of cytokines.

The invention also provides a method of inhibiting epithelial cancer comprising administering the composition to the subject, such that epithelial cancer is inhibited. Inhibition of the cancer includes (i) a reduction (e.g., by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%) in the number of epithelial cancer cells, (ii) prevention of an increase in the number of epithelial cancer cells, (iii) an increase (e.g., by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%) in apoptosis of epithelial cancer cells, and/or (iv) a decrease or plateau in solid tumor size.

The epithelial cancer can be any suitable cancer, including, but not limited to head and neck squamous cell carcinoma (HNSCC), ovarian cancer, cervical cancer, bladder cancer, esophageal cancer, gastric cancer, breast cancer, endometrial cancer, and colorectal (colon) cancer.

The polypeptide, nucleic acid, vector, and cell therapy can be used individually or in any combination. In addition, these treatments can be used as adjuncts to other treatments for epithelial cancer, such as hormone therapy, chemotherapy, surgery, cryosurgery, radiation therapy, and immunotherapy (e.g., anti-HER2 antibodies for breast cancer).

The invention also includes the administration of the polypeptide, nucleic acid, vector, cell, or composition thereof followed by a second administration (which may be the same or different) of the polypeptide, nucleic acid, vector, cell, or composition thereof as a "boost." The second administration can occur at any time frame, but is typically one to three months after the initial administration. The invention encompasses additional (e.g., one, two, three, or four) administrations following the first and second administrations as an additional "boost."

The following examples further illustrate the invention but, of course, should not be construed as in any way limiting its scope.

EXAMPLE 1

This example demonstrates the generation of the polypeptide of the invention.

Two polypeptides having a sequence of amino acids consisting of IXDFGLAKL (SEQ ID NO: 1) were synthesized using standard F-moc chemistry by the University of Pittsburgh Peptide Synthesis Facility. One polypeptide had a leucine at position 2 of SEQ ID NO: 1 and the other had a threonine at position 2 of SEQ ID NO: 1. The polypeptides were substantially pure, in that they were >90% pure as indicated by analytical HPLC and were validated by mass spectrometry. Lyophilized polypeptides were dissolved in 100% DMSO at a concentration of 2 mg/ml and stored at −20° C. until use.

It is interesting to note that $EGFR_{853-861}$ (i.e., SEQ ID NO: 1, wherein the residue at position 2 is threonine) shares identity with a HER-2 peptide that binds HLA-A*0201 and has demonstrated immunogenicity. In particular, $EGFR_{853-861}$ differs from the $HER2_{861-869}$ sequence at position 868.

EXAMPLE 2

This example describes a polypeptide-induced stabilization assay.

The polypeptide-induced stabilization assay of the HLA-A*0201 class I molecule expressed by the T2 cell line (a human T cell leukemia/B cell line hybrid) was performed using methods known in the art. Briefly, $5 \times 10^5$ T2 cells were incubated in the presence of 10-fold dilutions of polypeptide (i.e., $EGFR_{853-861}$, $EGFR_{853-861L}$, $HER2_{861-869}$, $Flu_{58-66}$, or $EGFR_{681-689}$) in AIM-V medium for 18 hours at 37° C. Surface HLA-A*0201 molecule expression was detected using the anti-HLA-A, -B, -C (W6/32) or anti-HLA-A2 mAb (BB7.2). After incubation with a FITC-conjugated secondary mAb, T2 cells were analyzed by flow cytometry using a FACScan (BD Biosciences).

The results of the experiment are set forth in FIG. 1.

EXAMPLE 3

This example demonstrates the immunogenicity of the inventive polypeptide.

Figure 6A:
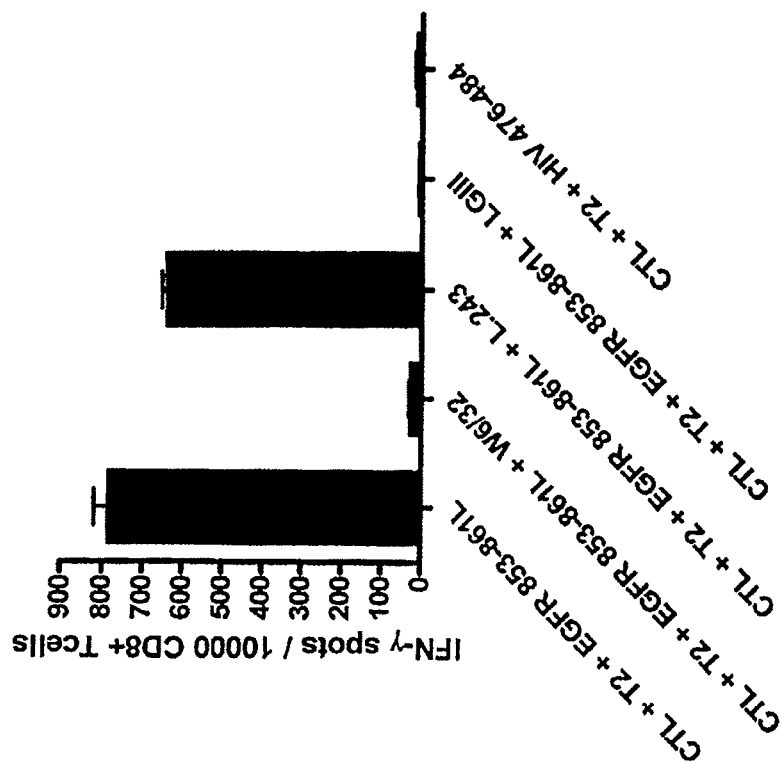
Figure 6B:
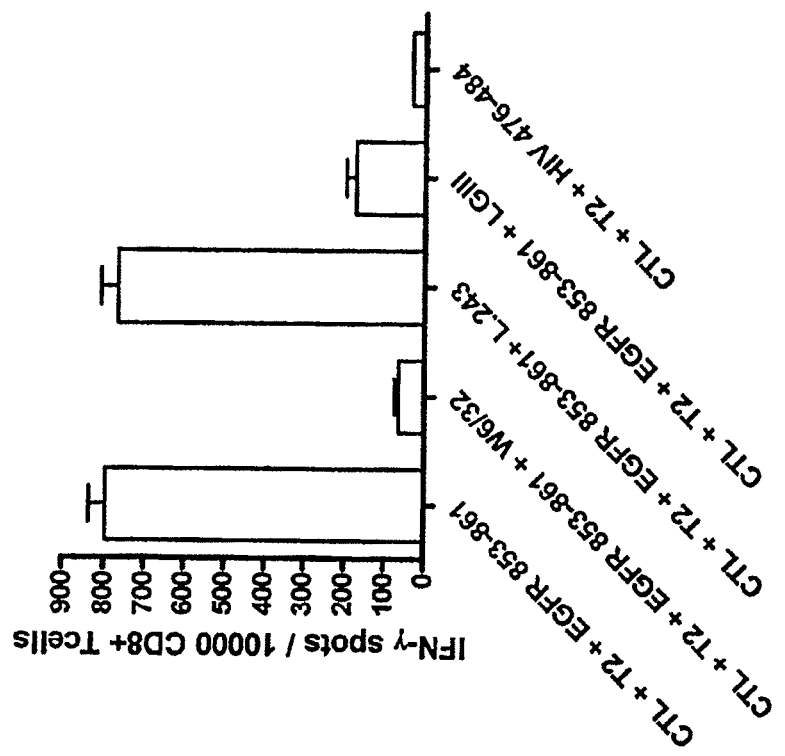

In vitro stimulation (IVS) was performed using $EGFR_{853-861}$ (i.e., SEQ ID NO: 1, wherein the residue at position 2 is threonine) or $EGFR_{853-861L}$ (i.e., SEQ ID NO: 1, wherein the residue at position 2 is leucine) to induce cytotoxic T lymphocytes (CTL) using CD8+PBMC from five HLA-A*0201+ healthy donors and one head and neck squamous cell carcinoma (SCCHN) patient. The resulting EGFR-specific CTL were tested for $EGFR_{853-861}$ specificity and HLA class I antigen restriction using polypeptide pulsed T2 cells. CTL generated against $EGFR_{853-861}$ polypeptide recognized T2 cells pulsed with either $EGFR_{853-861}$ or $EGFR_{853-861L}$ polypeptide, but not T2 cells alone or T2 cells incubated with the HIV $Pol_{476-484}$ polypeptide (10 μg/ml at 37° C.) (see FIGS. 6A and 6B). This CTL recognition of T2 cells, which only express HLA-A2 molecules, was blocked by incubation with the anti-HLA-A, -B, —C mAb W6/32 and the anti-HLA-A mAb LGIII.147.4 (see FIGS. 6A and 6B).

Figure 7:
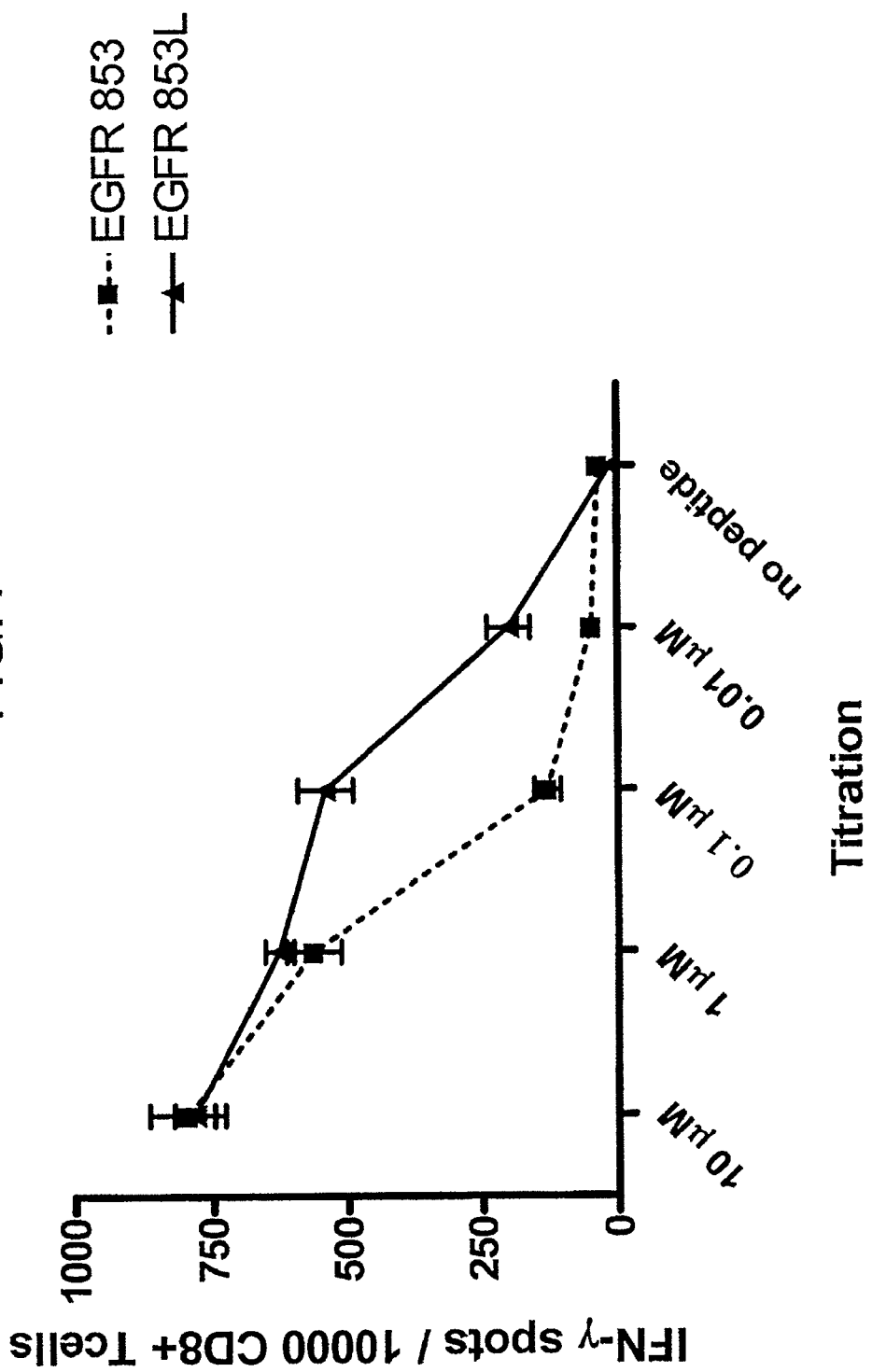
FIG. 7 depicts the results of an ELISPOT assay of CD8+ T cells against different concentrations of wild-type peptide (EGFR$_{853}$) and optimized peptide (EGFR$_{853L}$) loaded with T2 cells. The concentrations of peptides is indicated on the x-axis and the number of IFN-γ spots/5.0×10$^4$ CD8+ T cells is indicated on the y-axis.
Figure 8C:
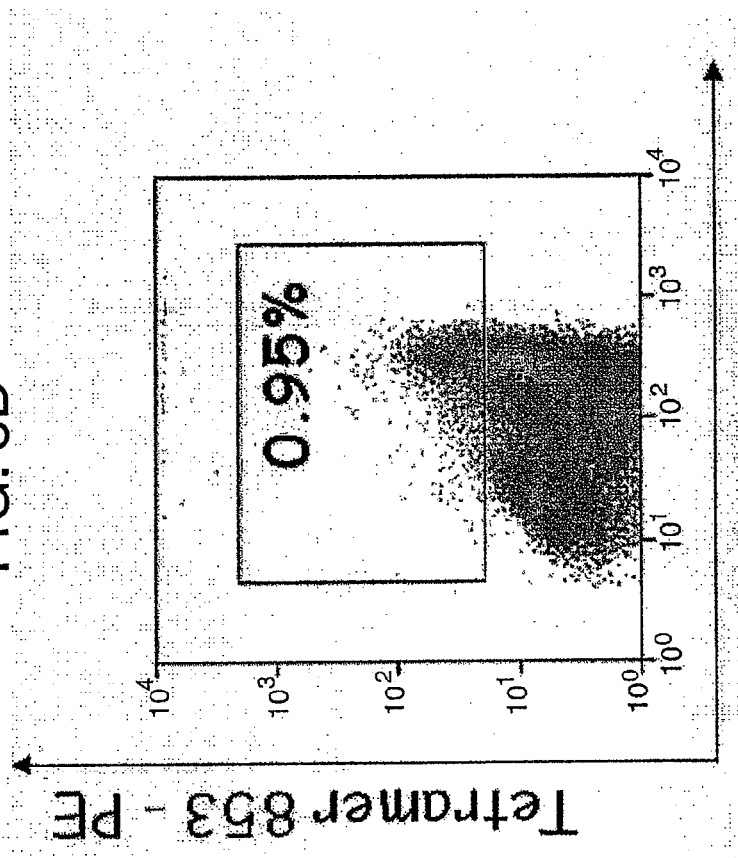
Figure 8D:
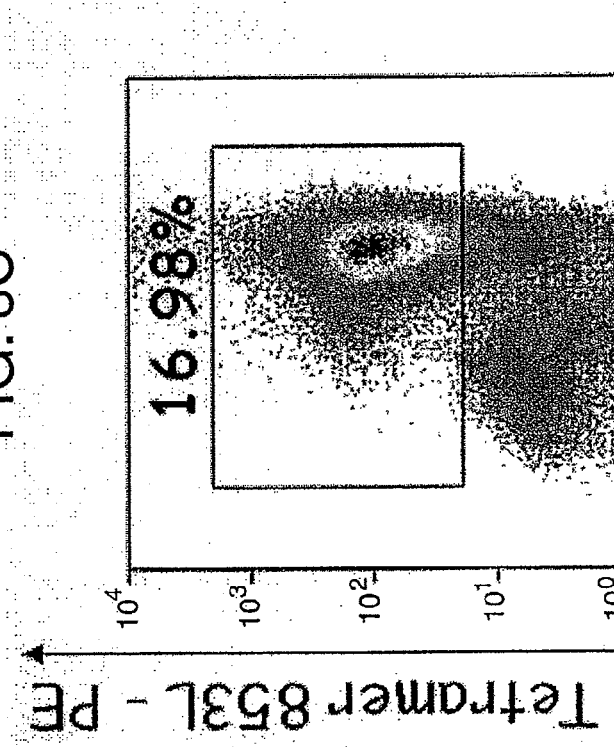

To compare the ability of $EGFR_{853-861}$ or $EGFR_{853-861L}$ polypeptide to stimulate $EGFR_{853-861}$ specific CTL, a peptide titration experiment was performed with ten-fold dilutions of $EGFR_{853-861}$ or $EGFR_{853-861L}$ polypeptide (see FIG. 7). Recognition of T2 cells incubated with the $EGFR_{853-861L}$ polypeptide was detectable at approximately 20-fold lower concentrations than CTL recognition of T2 cells incubated with $EGFR_{853-861}$ polypeptide (see FIG. 7), indicating improved immunogenicity of the $EGFR_{853-861L}$ polypeptide, which is potentially due to enhanced HLA-A*0201 binding and/or stabilization.

CTL derived from $EGFR_{853-861}$ or $EGFR_{853-861L}$ polypeptide, as well as a HER2 encoded polypeptide ($HER2_{861-869}$; ITDFGLARL; SEQ ID NO: 3), demonstrated cross-reactivity, which supports the therapeutic application of EGFR family-targeted vaccine approaches.

EXAMPLE 4

This example describes the purification of T cells comprising the polypeptide of the invention using HLA-A2/peptide tetrameric complexes (tetramer).

The PE-labeled HLA-A*0201 $EGFR_{853-861}$ and HLA-A*0201 $EGFR_{853-861L}$ tetramers were obtained from the Tetramer Facility of the National Institute of Allergy and Infectious Disease (Atlanta, Ga.). Specificity was confirmed by staining of the CTL line specific for each polypeptide after IVS and the lack of staining of irrelevant (e.g., $MAGE-3_{271-279}$ specific) CTL or HLA-A2− PBMCs obtained from normal donors. Three-color flow cytometry assays (FACScan; BD Biosciences) were performed with energy-coupled dye labeled anti-CD3 and FITC-anti-CD8 Abs (Beckman Coulter) and PE-tetramer. Flow cytometry was performed on a CyAn™ flow cytometer (Dako, Ft. Collins, Colo.) machine, and data analyzed using Summit V4.3 software. Generally, 100,000 events per sample were collected after gating on lymphocytes by forward- and side-scatter. CTL clones were sorted using PE-labeled HLA-A2EGFR$_{853-861}$ polypeptide loaded tetramers. Clones were plated in 96-well-U-bottom plates and 50 of cytokine stimulation mixture was added. IVS was performed using $10^6$ allogeneic PBLs/ml with a concentration of 5×10⁶ per plate, and irradiated with 50 Gy, IL-2 at 200 IU/ml and PHA-L at 1 µg/ml. The clones were restimulated every 7 to 10 days with 50 µl of stimulation mixture.

EXAMPLE 5

This example describes the induction of CD8⁺ T cells with the polypeptide of the invention.

PBMCs were isolated by density centrifugation on Ficoll-Paque™ PLUS (GE Healthcare Bio-Science AB; SE-751 84 Uppsala) and used to prepare mature DCs using methods described in the art. PBMCs were resuspended at 5×10⁷/ml in AIM-V medium (Invitrogen) and were incubated for 90 min in 75-cm² tissue culture flasks or six-well plates (37° C.; 5% $CO_2$). Non-adherent (T cell-enriched) cells were gently washed out with HBSS and subsequently frozen. The plastic adherent cells were cultured in AIM-V medium supplemented with 1000 units/ml rhGM-CSF and 1000 units/ml rhIL-4. Six days later, the culture medium was removed, and the immature DCs were cultured in AIM-V supplemented with 1000 units/ml rhGM-CSF and 1000 units/ml rhIL-4, 10 ng/ml rhIL-6, 10 ng/ml recombinant human tumor necrosis factor (TNF)-α, and 10 ng/ml IL-1β and 1 µg/ml $PGE_2$. Mature DCs were harvested on day 8, centrifuged and frozen or used to stimulate autologous T cells. The stimulator cells were resuspended in AIM-V at 10⁶/ml supplemented with 10 µg/ml of each polypeptide ($EGFR_{853-861}$ and $EGFR_{853-861L}$) and incubated for 4 hours at 37° C. The polypeptide-pulsed DCs were then irradiated (50 Gy) and washed and resuspended in culture medium (Iscove's medium supplemented with 10% human serum, L-arginine, L-asparagine, and L-glutamine). Autologous CD8⁺ T cells were negatively isolated from PBMCs with immunomagnetic beads (Miltenyi Biotech, Germany) and added to the polypeptide-pulsed DCs at a ratio of 1×10⁶ cell/ml to 1×10⁵ polypeptide-pulsed DC in a final volume of 2 ml of culture medium (24-well tissue culture plate). The cells were cultured for 48 hours at 37° C. with IL-2 (20 units/ml) and IL-7 (5 ng/ml). On day 7 and weekly thereafter, lymphocytes were restimulated with autologous irradiated DCs pulsed with polypeptide in culture medium supplemented with 20 units/ml IL-2 and 5 ng/ml IL-7. The stimulated CD8⁺ T cells were analyzed for specificity in IFN-γ ELISPOT and ⁵¹Cr release assays at day 21 and then every 7 days thereafter.

EXAMPLE 6

This example describes the assessment of T cell responses to the polypeptide of the invention and tumor cells.

The recognition of APCs pulsed with polypeptide ($EGFR_{853-861}$ or $EGFR_{853-861L}$) and head and neck tumor cells was assessed by ELISPOT assays specific for hu-IFN-γ. For the ELISPOT assays, multiscreen HTS plates (Millipore, Bedford, Mass.) were coated with 10 µg/ml of either mAb antihuman IFN-γ (1-D1K; Mabtech, Stockholm, Sweden) in PBS (Life Technologies, Inc.) overnight at 4° C. Unbound mAb was removed by four successive washings with PBS. After the plates were blocked with Iscove's modified Dulbecco's Medium with 10% human serum (1 hour at 37° C.), CD8⁺ T cells were seeded in triplicate (5×10⁴ for bulk CD4⁺ T cells and 10³ for CD8⁺ T cell clones) in multiscreen HTS plates. Nonirradiated T2 cells (5×10⁴) or SCC4, PCI-30, or PCI-13 head and neck tumor cell lines (5×10⁴) were added. Synthetic polypeptides were then added into ELISPOT assays after APCs were seeded. Control wells contained unstimulated T cells, T cells in the presence of unloaded T2 cells, or tumor cells alone. Culture medium was AIM-V at a final volume of 200 µl/well.

After incubation at 37° C. in 5% $CO_2$ for 40 hours (IFN-γ ELISPOT assays), cells were removed by washings with PBS-0.05% Tween 20 (PBS-T). Captured cytokine was detected at sites of its secretion by incubation for 4 hours with biotinylated mAb anti-hIFN-γ (7-B6-1; Mabtech) at 2 µg/ml in PBS-0.5% BSA. Plates were washed six times with PBS-T, and avidin-peroxidase complex, diluted 1:100 (Vectastain Elite Kit: Vector, Burlingame, Calif.), was added for 1 hour at room temperature. Unbound complex was removed by three successive washings with PBS-T and three with PBS alone. Peroxidase staining was performed with 3,3,5'-tetramethylbenzidine (Vector Laboratories) for 4 minutes and stopped by rinsing the plates under running tap water. Spot numbers and spot sizes were automatically determined with the use of computer-assisted video image analysis.

Figure 2A:
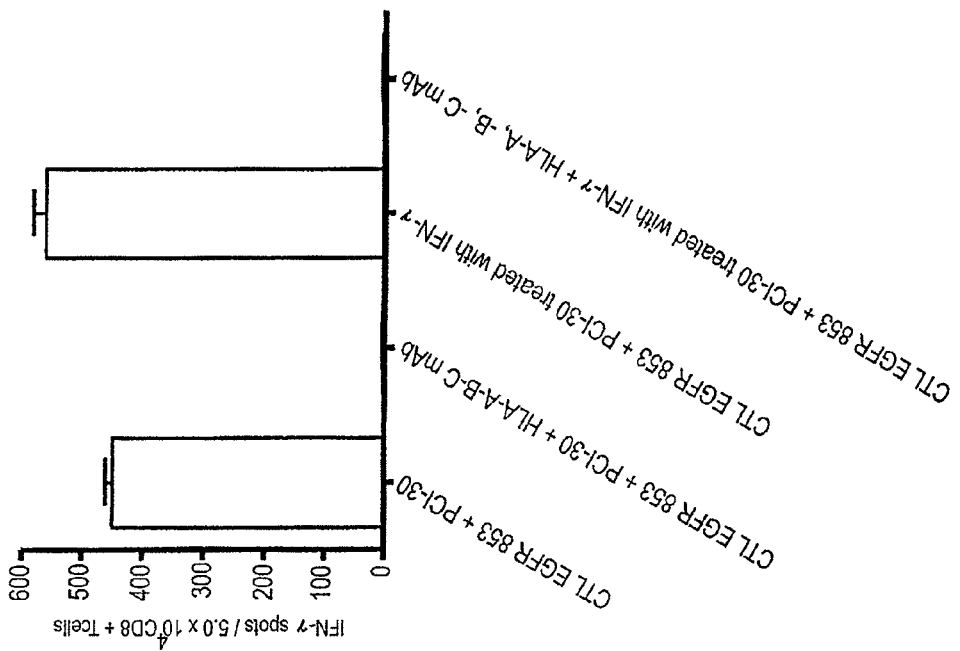
Figure 2B:
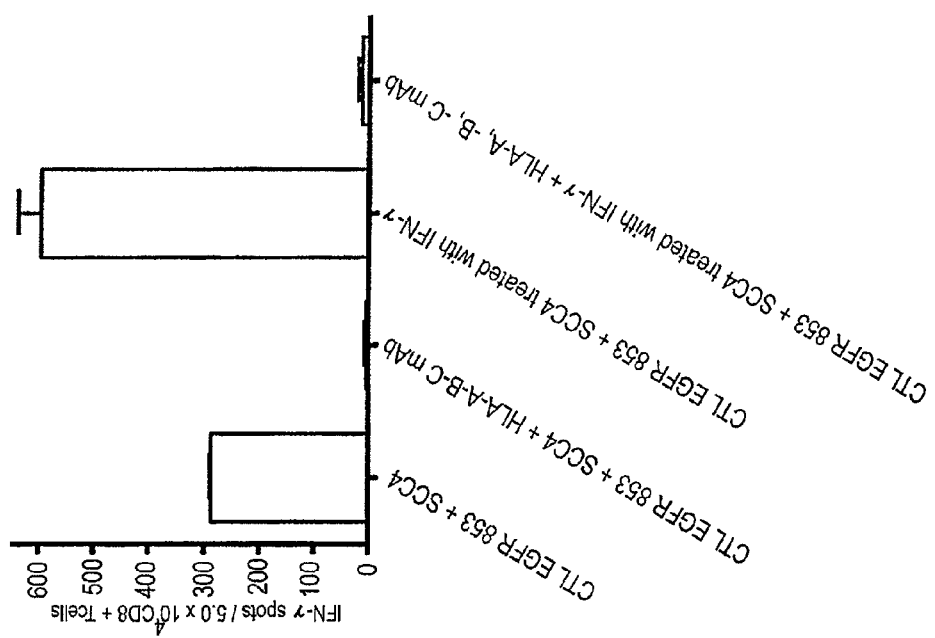
Figure 3:
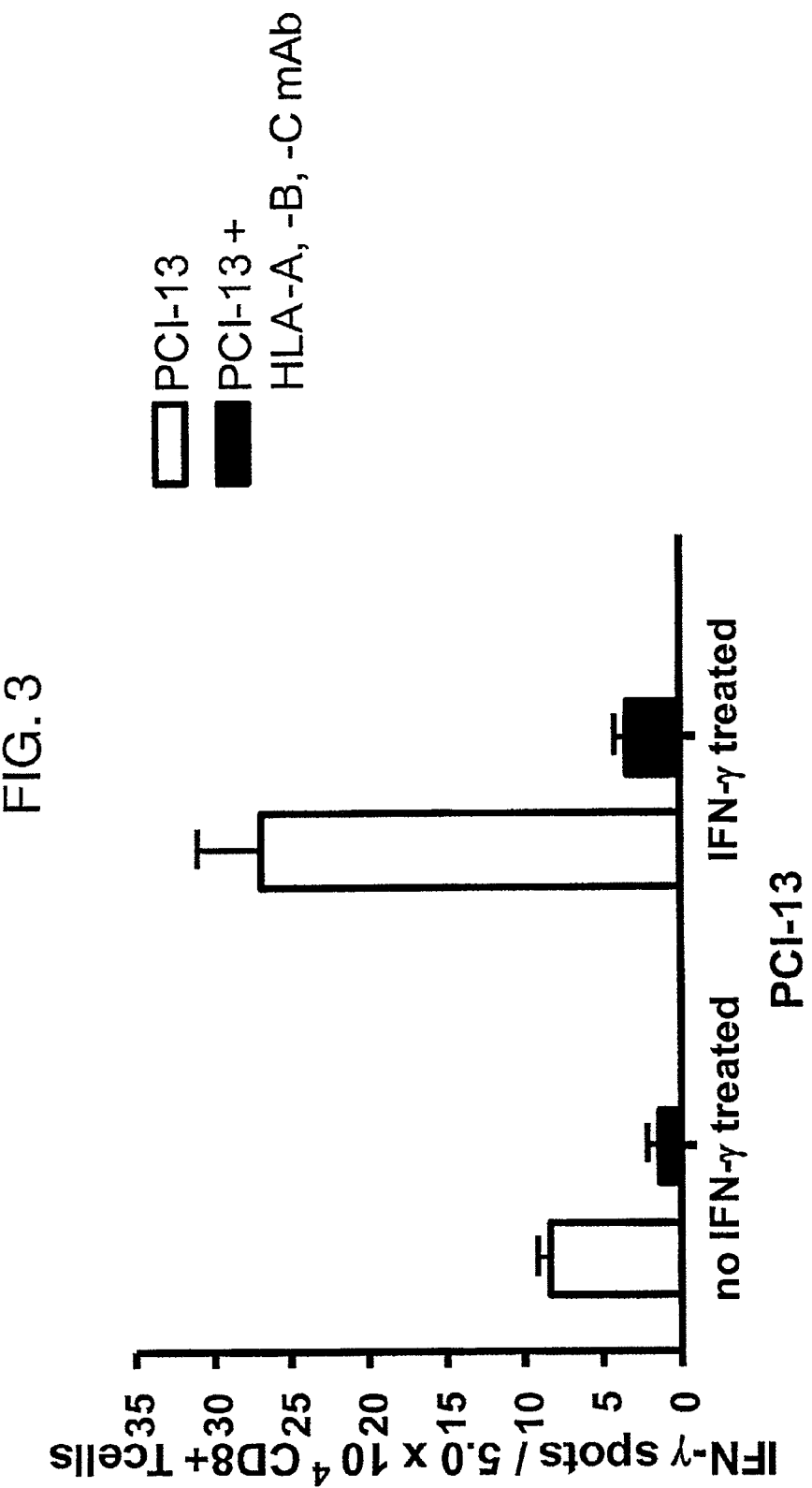

The stimulated CD8⁺ T cells recognized the HLA-A2⁺ head and neck tumor cells, SCC4, PCI-30, and PCI-13, as indicated by the amount of IFN-γ spots in the ELISPOT assay. For SCC4 cells, there were about 300 IFN-γ spots/5×10⁴ CD8⁺ T cells and about 600 IFN-γ spots/5×10⁴ CD8⁺ T cells when the SCC4 cells were treated with IFN-γ (see FIGS. 2A and 9A). For PCI-30 cells, there were about 450 IFN-γ spots/5×10⁴ CD8⁺ T cells and about 550 IFN-γ spots/5×10⁴ CD8⁺ T cells when the PCI-30 were treated with IFN-γ (see FIGS. 2B and 9A). For PCI-13 cells, there were about 8 IFN-γ spots/5×10⁴ CD8⁺ T cells and about 27 IFN-γ spots/5×10⁴ CD8⁺ T cells when the PCI-13 cells were treated with IFN-γ (see FIGS. 3 and 9A). Little or no spots were detected following the additions of HLA-A, -B, and -C mAb, demonstrating T cell reactivity in an HLA dependent manner (see FIGS. 2A, 2B, 3, and 9A).

Figure 4:
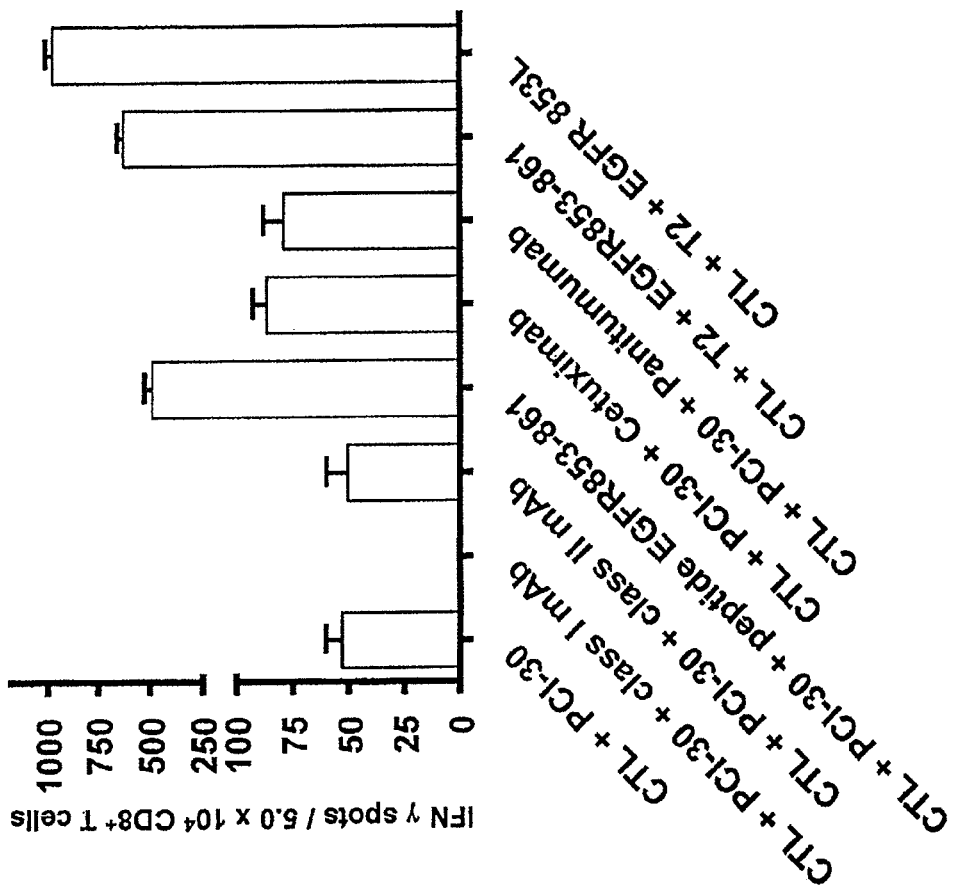

To provide further evidence that the polypeptide of the invention is a class I restricted epitope, class I and class II mAb were separately added to compositions comprising CTLs (stimulated with $EGFR_{853-861}$) and PCI-30 cells. Addition of the class II mAb resulted in no change in the amount of IFN-γ spots/5×10⁴ CD8⁺ T cells; however, no spots were detected following the addition of the class I mAb (see FIGS. 4 and 10). The addition of anti-EGFR antibody (cetuximab or panitumumab) increased the number of IFN-γ spots (FIGS. 4 and 10). Similarly, addition of the polypeptide of the invention ($EGFR_{853-861}$ or $EGFR_{853-861L}$) resulted in a significant increase in IFN-γ spots (see FIG. 4).

EXAMPLE 7

This example describes the generation of a vector comprising a nucleic acid encoding the polypeptide of the invention.

A nucleic acid encoding the polypeptide of the invention is inserted under the control of the vaccinia 40K promoter (see, e.g., Gritz et al., *J. Virol.*, 64: 5948-5957 (1990)) into the HindIII M genomic region of the Wyeth strain of vaccinia virus. A selection marker, such as the lacZ gene, can be used to identify recombinant viruses. For example, the *E. coli* lacZ gene, under the control of the fowlpox C1 promoter (see, e.g., Jenkins et al., *AIDS Res. Hum. Retroviruses*, 7: 991-998 (1991)) can be included as a calorimetric marker for recombinant viruses. Then, recombinant viruses can be identified using a chromogenic assay for the lacZ gene product.

1×10⁶ immune cells (e.g., DCs, APCs, lymphocytes, etc.) are incubated with the recombinant virus encoding the polypeptide of the invention. Titration experiments are performed to determine the amount of virus necessary to consistently induce production of the polypeptide of the invention.

The infected cells are suspended in 10 ml RPMI-1640 complete medium containing 100 ng/ml of rhGM-CSF, 20 ng/ml rhIL-4, and 20 ng/ml of TNF-alpha cultured for 24 hours.

EXAMPLE 8

This example demonstrates that the treatment with an EGFR-specific antibody enhances $EGFR_{853-861}$-specific T cell recognition.

It has been suggested that treatment of tumor cells by EGFR-specific mAb induces resistance through internalization and degradation of EGFR from the cell surface (Lu et al., *Cancer Res.*, 67: 8240-8247 (2007)). Whether cetuximab treatment of SCCHN cells causes internalization and degradation of EGFR from the cell surface, resulting in elevated levels of HLA-A*0201-$EGFR_{853-861}$ peptide complexes, as measured by CTL recognition, was investigated.

To test whether EGFR-specific mAb treatment of SCCHN cells enhanced $EGFR_{853-861}$-specific CTL recognition, PCI-30 SCCHN cells were treated with cetuximab (10 μg/mL for 18 hours at 37° C.), isotype matched control IgG1 mAb, or media alone, and then tested for $EGFR_{853-861}$-specific CTL recognition in IFN-γ ELISPOT assays (see FIG. 12).

$EGFR_{853-861}$ peptide-specific CTL recognition of PCI-30 cells was significantly enhanced after incubation with cetuximab ($P \leq 0.05$), but not with control mAb IgG1. In addition, EGFR protein levels were reduced in PCI-30 cells that were treated for 2 or 6 hours with cetuximab (10 μg/mL at 37° C.) as measured by Western blot.

These results signify that cetuximab treatment of tumor cells (e.g., SCCHN) leads to EGFR degradation and enhanced $EGFR_{853-861}$-specific CTL recognition.

EXAMPLE 9

This example demonstrates that there is enhancement by cetuximab of EGFR-specific cross-presentation by dendritic cells (DC) incubated with tumor cells.

Immature DC generated from HLA-A*201+ healthy donor plastic-adherent monocytes were incubated for 36 hours at 37° C. with UV-irradiated HLA-A*0201−, EGFR+ PCI-15B tumor cells, and either cetuximab (10 μg/mL) or isotype-matched control IgG1 mAb (10 μg/mL). DC matured under these conditions were used as targets in an IFN-γ ELISPOT using $EGFR_{853-861}$-specific CTL as effectors (see FIG. 13).

In an additional experiment, immature DC generated from healthy donor PBMC were incubated for 24 hours at 37° C. with UV-irradiated PCI-15B tumor cells treated with cetuximab (10 μg/ml) with or without the addition of autologous NK cells (FcγR IIIa V/F genotype). Tumor cells not treated with cetuximab or treated with isotype-matched IgG1, or those incubated with or without NK cells, were used as controls. DC matured for 48 hour were used as targets in an IFN-γ ELISPOT or flow cytometry quantification using $EGFR_{853-861}$ specific CTL as effectors (see FIGS. 14A-B).

These experiments illustrate that enhanced tumor antigen (i.e., EGFR)-specific cross-presentation by DC results after incubation with cetuximab-activated NK:PCI-15B cells.

EXAMPLE 10

This example demonstrates that that EGFR-specific CTL are induced in the circulation of cetuximab-treated SCCHN patients.

To determine whether cetuximab enhances cross-presentation of EGFR peptides by DC in vivo, PBMC were obtained from 17 HLA-A*0201+ cetuximab-treated and 39 HLA-A*0201+ cetuximab-naïve SCCHN patients. CD8+ T cells were stained with $EGFR_{853-861}$-specific tetramers to quantitate the frequency of circulating $CD3^+CD8^+$ T cells specific for this EGFR epitope. $EGFR_{853-861}$ tetramer staining of $CD3^+CD8^+$ T cells was performed using flow cytometry. The negative control HIV tetramer was used to stain both cetuximab-treated and naïve SCCHN patient PBMC.

As evidenced by FIGS. 15A-B, EGFR-specific tetramer+ T cell frequencies are elevated in cetuximab-treated HNC patients compared to cetuximab-naïve HNC patients. A significantly higher frequency of EGFR-specific T cells was found in PBMC from HLA-A*0201+ cetuximab-treated SCCHN patients than in PBMC from HLA-A*0201+ cetuximab-naïve SCCHN patients ($p<0.0022$, two-tailed, Wilcoxon test). No significant staining of T cells was observed using a negative control tetramer that binds to HIV-1 ($pol_{478-484}$)-specific T cells or using PBMC from HLA-A*0201− SCCHN patients. Background tetramer staining was observed with control PBMC from HLA-A*0201+ cetuximab-naïve SCCHN patients. Tetramer staining of both cetuximab-treated and -naïve SCCHN patients was performed for negative control, HIV-1 ($pol_{478-484}$)-specific T cells to exclude a nonspecific antigen effect after cetuximab treatment.

These data strongly support that the administration of cetuximab to SCCHN patients leads to $EGFR_{853-861}$ peptide cross-presentation by DC, triggering an expansion of EGFR-specific T cells.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated or substantially purified polypeptide consisting of (SEQ ID NO: 1).

2. A composition comprising a polypeptide consisting of SEQ ID NO: 1 and a carrier.

3. The composition of claim 2, further comprising an adjuvant.

4. The composition of claim 3, wherein the adjuvant is selected from the group consisting of IL-1-beta, IL-2, IL-4, IL-6, IL-7, IL-12, IL-15, IL-21, PGE, RANTES, GM-CSF, TNF-alpha, IFN-gamma, incomplete Freund's adjuvant, alum, aluminum salts, aluminum phosphate, aluminum hydroxide, aluminum silica, Montanide, calcium phosphate, and combinations thereof.

5. The composition of claim 2, further comprising a chemotherapeutic agent.

6. The composition of claim 5, wherein the chemotherapeutic agent is an EGFR family-specific antibody.

7. The composition of claim 6, wherein the EGFR family-specific antibody is cetuximab.

8. The composition of claim 2, further comprising a tumor associated antigen selected from the group consisting of MAGE, p53, ErbB2, MUC-1, HAGE, and human papilloma virus.

9. The composition of claim 2, wherein the composition is a pharmaceutical composition and the carrier is a pharmaceutically acceptable carrier.

10. A method of inducing a cytotoxic T lymphocyte response in a patient with epithelial cancer cells expressing EGFR, comprising administering to the patient the composition of claim, such that a T cell cytotoxic T lymphocyte response against the epithelial cancer is induced.

* * * * *

UNITED STATES PATENT AND TRADEMARK OFFICE
CERTIFICATE OF CORRECTION

PATENT NO. : 8,367,069 B2
APPLICATION NO. : 12/959073
DATED : February 5, 2013
INVENTOR(S) : Ferris et al.

Page 1 of 1

It is certified that error appears in the above-identified patent and that said Letters Patent is hereby corrected as shown below:

In the Claims

In column 24, lines 42-46: replace "A method of inducing a cytotoxic T lymphocyte response in a patient with epithelial cancer cells expressing EGFR, comprising administering to the patient the composition of claim, such that a T cell cytotoxic T lymphocyte response against the epithelial cancer is induced." with -- A method of inducing a cytotoxic T lymphocyte response in a patient with epithelial cancer cells expressing EGFR, comprising administering to the patient the composition of claim 2, such that a cytotoxic T lymphocyte response against the epithelial cancer is induced. --

Signed and Sealed this
Seventh Day of May, 2013

Teresa Stanek Rea
*Acting Director of the United States Patent and Trademark Office*

```
                        SEQUENCE LISTING

<160> NUMBER OF SEQ ID NOS: 3

<210> SEQ ID NO 1
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: X can be threonine or leucine

<400> SEQUENCE: 1

Ile Xaa Asp Phe Gly Leu Ala Lys Leu
1               5

<210> SEQ ID NO 2
<211> LENGTH: 1210
<212> TYPE: PRT
<213> ORGANISM: Homo sapiens

<400> SEQUENCE: 2

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255
```

-continued

Glu Ala Thr Cys Lys Asp Thr Cys Pro Pro Leu Met Leu Tyr Asn Pro
                260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Cys Glu Gly Pro Cys Arg Lys Val
                325                 330                 335

Cys Asn Gly Ile Gly Ile Gly Glu Phe Lys Asp Ser Leu Ser Ile Asn
                340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
                420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
            515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
            565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
    595                 600                 605

Lys Tyr Ala Asp Ala Gly His Val Cys His Leu Cys His Pro Asn Cys
        610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
    675                 680                 685

```
Val Glu Pro Leu Thr Pro Ser Gly Glu Ala Pro Asn Gln Ala Leu Leu
    690                 695                 700

Arg Ile Leu Lys Glu Thr Glu Phe Lys Ile Lys Val Leu Gly Ser
705                 710                 715                 720

Gly Ala Phe Gly Thr Val Tyr Lys Gly Leu Trp Ile Pro Glu Gly Glu
                    725                 730                 735

Lys Val Lys Ile Pro Val Ala Ile Lys Glu Leu Arg Glu Ala Thr Ser
                740                 745                 750

Pro Lys Ala Asn Lys Glu Ile Leu Asp Glu Ala Tyr Val Met Ala Ser
            755                 760                 765

Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
                820                 825                 830

Leu Val His Arg Asp Leu Ala Ala Arg Asn Val Leu Val Lys Thr Pro
            835                 840                 845

Gln His Val Lys Ile Thr Asp Phe Gly Leu Ala Lys Leu Leu Gly Ala
        850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
                900                 905                 910

Lys Pro Tyr Asp Gly Ile Pro Ala Ser Glu Ile Ser Ser Ile Leu Glu
            915                 920                 925

Lys Gly Glu Arg Leu Pro Gln Pro Pro Ile Cys Thr Ile Asp Val Tyr
930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
        995                 1000                1005

Asp Val Val Asp Ala Asp Glu Tyr Leu Ile Pro Gln Gln Gly Phe
    1010                1015                1020

Phe Ser Ser Pro Ser Thr Ser Arg Thr Pro Leu Leu Ser Ser Leu
    1025                1030                1035

Ser Ala Thr Ser Asn Asn Ser Thr Val Ala Cys Ile Asp Arg Asn
    1040                1045                1050

Gly Leu Gln Ser Cys Pro Ile Lys Glu Asp Ser Phe Leu Gln Arg
    1055                1060                1065

Tyr Ser Ser Asp Pro Thr Gly Ala Leu Thr Glu Asp Ser Ile Asp
    1070                1075                1080

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
```

-continued

```
             1100                1105                 1110

Pro Leu Asn Pro Ala Pro Ser Arg Asp Pro His Tyr Gln Asp Pro
    1115                1120                1125

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205                1210

<210> SEQ ID NO 3
<211> LENGTH: 9
<212> TYPE: PRT
<213> ORGANISM: Artificial Sequence
<220> FEATURE:
<223> OTHER INFORMATION: Synthetic

<400> SEQUENCE: 3

Ile Thr Asp Phe Gly Leu Ala Arg Leu
1               5
```